(12) United States Patent
Jung et al.

(10) Patent No.: US 11,804,285 B2
(45) Date of Patent: Oct. 31, 2023

(54) HILBERT-CNN: AI-DRIVEN CONVOLUTIONAL NEURAL NETWORKS WITH CONVERSION DATA OF GENOME FOR BIOMARKER DISCOVERY

(71) Applicant: SYNTEKABIO, INC., Daejeon (KR)

(72) Inventors: Jongsun Jung, Daejeon (KR); Jaeyun Yoo, Daejeon (KR); Jaemin Seol, Daejeon (KR)

(73) Assignee: SYNTEKABIO, INC., Daejeon (KR)

( * ) Notice: Subject to any disclaimer, the term of this patent is extended or adjusted under 35 U.S.C. 154(b) by 1310 days.

(21) Appl. No.: 16/198,201

(22) Filed: Nov. 21, 2018

(65) Prior Publication Data

US 2019/0180844 A1   Jun. 13, 2019

(30) Foreign Application Priority Data

Sep. 25, 2017 (KR) .................... 10-2017-0123731
Dec. 31, 2017 (KR) .................... 10-2017-0185041

(51) Int. Cl.
| | |
|---|---|
| *G16B 40/00* | (2019.01) |
| *G06N 3/08* | (2023.01) |
| *G16B 40/20* | (2019.01) |
| *G16B 20/40* | (2019.01) |
| *G16B 20/00* | (2019.01) |
| *G06N 3/045* | (2023.01) |

(52) U.S. Cl.
CPC ............. *G16B 40/00* (2019.02); *G06N 3/045* (2023.01); *G06N 3/08* (2013.01); *G16B 20/00* (2019.02); *G16B 20/40* (2019.02); *G16B 40/20* (2019.02)

(58) Field of Classification Search
CPC ...... G16B 40/00; G16B 40/20; G06N 3/0454; G06N 3/08
USPC ........................................................ 702/20
See application file for complete search history.

(56) References Cited

U.S. PATENT DOCUMENTS

| | | |
|---|---|---|
| 7,167,856 B2 | 1/2007 | Lawder |
| 7,245,196 B1 | 7/2007 | Baliarda et al. |
| 2011/0150140 A1 | 6/2011 | Alexopoulos et al. |

OTHER PUBLICATIONS

Yuan, Y., Shi, Y., Li, C. et al. DeepGene: an advanced cancer type classifier based on deep learning and somatic point mutations. BMC Bioinformatics 17, 476 (2016). (Year: 2016).*
Emmanuel Adetiba, Oludayo O. Olugbara, "Lung Cancer Prediction Using Neural Network Ensemble with Histogram of Oriented Gradient Genomic Features", The Scientific World Journal, vol. 2015, Article ID 786013, 17 pages, 2015. (Year: 2015).*

(Continued)

*Primary Examiner* — Larry D Riggs, II
*Assistant Examiner* — Guozhen Liu
(74) *Attorney, Agent, or Firm* — ArentFox Schiff LLP

(57) ABSTRACT

A method of detecting biomarkers using an artificial intelligence (AI) deep learning model for conversion data of nucleotide sequences and mutations of population genomes, the method including: collecting nucleotide sequences and mutations of population genomes; generating conversion data by reflecting mutations of diploid genomes in the collected nucleotide sequences; performing an artificial intelligence (AI) deep learning model with the generated conversion data; generating a fully connected network (FCN) by connecting the results obtained by the machine learning; and extracting biomarkers by the learned model.

12 Claims, 25 Drawing Sheets

Specification includes a Sequence Listing.

Prediction of mutation biomarkers, disease-associated biomarkers and patient stratification biomarkers

(56) References Cited

OTHER PUBLICATIONS

X.-B. Wei et al., "CCDC26 Gene Polymorphism and Glioblastoma Risk in the Han Chinese Population," Asian Pacific Journal of Cancer Prevention, vol. 15, No. 8. Asian Pacific Organization for Cancer Prevention, pp. 3629-3633, Apr. 30, 2014. (Year: 2014).*
Jan Smrek, Alexander Y. Grosberg: A novel family of space-filling curves in their relation to chromosome conformation in eukaryotes, Physica A: Statistical Mechanics and its Applications, vol. 392, Issue 24, 2013, p. 6375-6388 (Year: 2013).*
Christof Angermueller, Tanel Pärnamaa, Leopold Parts, Oliver Stegle: Deep learning for computational biology, Molecular Systems Biology (2016)12:878. (Year: 2016).*
H Hu: F-Curve, a graphical representation of protein sequences for similarity analysis based on physicochemical properties of amino acids, Match Commun. Math. Comput. Chem. 73 (2015) 749-764 (Year: 2015).*
Zhou, J and Troyanskaya, OG: ("Predicting effects of noncoding variants with deep learning-based sequence model". Nat Methods 12, 931-934 (2015)). (Year: 2015).*
Korean Office Action for related KR application No. 10-2017-0185041 dated Mar. 19, 2018 from Korean Intellectual Property Office.
Korean Office Action for related KR application No. 10-2017-0185041 dated Jul. 30, 2018 from Korean Intellectual Property Office.
Prateek Kumar et al. "Predicting the effects of coding non-synonymous variants on protein function using the SIFT algorithm", Nature Protocols, Jun. 25, 2009, pp. 1073-1082, vol. 4, No. 8.
Ivan A Adzhubei et al. "A method and server for predicting damaging missense mutations", Nature Methods, Apr. 2010, pp. 248-249, vol. 7, No. 4.
Sung Chun et al. "Identification of deleterious mutations within three human genomes", Genome Research, 2009, pp. 1553-1561, vol. 19.
Ryia-Illani Mohd Yunos et al. "Characterisation of genomic alterations in proximal and distal colorectal cancer patients", Peer J Preprints, Jun. 7, 2016, pp. 1-34.
Boris Reva et al. "Predicting the functional impact of protein mutations: application to cancer genomics", Nucleic Acids Research, Jul. 3, 2011, pp. 1-14, vol. 39, No. 17.
Florian Gnad et al. "Assessment of computational methods for predicting the effects of missense mutations in human cancers", BMC Genomics, May 28, 2013, pp. 1-13, vol. 14, No. S7.
Chengliang Dong et al. "Comparison and integration of deleteriousness prediction methods for nonsynonymous SNVs in whole exome sequencing studies", HMG Advance Access, Dec. 30, 2014, pp. 1-35.
Maho Oishi et al. "Comprehensive molecular diagnosis of a large cohort of Japanese retinitis pigmentosa and Usher syndrome patients by next-generation sequencing", Investigative Ophthalmology & Visual Science, Oct. 16, 2014, pp. 1-25.
Katherine S. Pollard et al. "Detection of nonneutral substitution rates on mammalian phylogenies", Genome Research, Jan. 2010, pp. 110-121, vol. 20.
Eugene V. Davydov et al. "Identifying a High Fraction of the Human Genome to be under Selective Constraint Using GERP++", PLoS Computational Biology, Dec. 2010, pp. 1-14, vol. 6, Issue 12.
Hitoshi Tsuda et al. "HER2 testing on core needle biopsy specimens from primary breast cancers: interobserver reproducibility and concordance with surgically resected specimens", BMC Cancer, 2010, pp. 1-11, vol. 10, No. 534.
Manuel Garber et al. "Identifying novel constrained elements by exploiting biased substitution patterns", Bioinformatics, Jun. 15, 2009, pp. i54-i62, vol. 25.
Hannah Carter et al. "Prioritization of driver mutations in pancreatic cancer using cancer-specific high-throughput annotation of somatic mutations (CHASM)", Cancer Biology & Therapy, Sep. 15, 2010, pp. 582-587, vol. 10, No. 6.
Fabio Vandin et al. "De novo discovery of mutated driver pathways in cancer", Genome Research, Jun. 7, 2011, pp. 375-385, vol. 22.
Michael S. Lawrence et al. "Mutational heterogeneity in cancer and the search for new cancer-associated genes", Nature, Jul. 11, 2013, pp. 214-218, vol. 499.
Hashem A. Shihab et al. "Predicting the Functional, Molecular, and Phenotypic Consequences of Amino Acid Substitutions using Hidden Markov Models", Human Mutation, Oct. 2012, pp. 57-65, vol. 34, No. 1.
Hannah Carter et al. "Identifying Medelian disease genes with the Variant Effect Scoring Tool", BMC Genomics, 2013, pp. 1-16, vol. 14, No. 53.
Alice B. Djotsa Nono et al. "Computational Prediction of Genetic Drivers in Cancer", eLS, Feb. 2016, pp. 1-30.
Martin Kircher et al. "A general framework for estimating the relative pathogenicity of human genetic variants", Nature Genetics, Feb. 2, 2014, pp. 1-8.
K. Joeri Van Der Velde et al. "Evaluation of CADD Scores in Curated Mismatch Repair Gene Variants Yields a Model for Clinical Validation and Prioritization", Human Mutation, Apr. 2015, pp. 712-719, vol. 36, No. 7.
Cheryi A. Mather, MD et al. "CADD score has limited clinical validity for the identification of pathogenic variants in noncoding regions in a hereditary cancer panel", Genetics in Medicine, May 5, 2016, pp. 1-7.
Runjun D Kumar et al. "Unsupervised detection of cancer driver mutations with parsimony-guided learning", Nature Genetics, Oct. 2016, pp. 1288-1298, vol. 48, No. 10.
Christof Angermueller et al. "DeepCpG: accurate prediction of single-cell DNA methylation states using deep learning", Genome Biology, Apr. 2017, pp. 1-13, vol. 18, No. 67.
Aparajita Dutta et al. "SpliceVec: Distributed feature representations for splice junction prediction", Computational Biology and Chemistry, Mar. 2018, pp. 1-8.
Zuguang Gu et al. "HilbertCurve: an R/Bioconductor package for high-resolution visualization of genomic data", Bioinformatics, Mar. 24, 2016, pp. 1-3.
Simon Anders "Visualization of genomic data with the Hilbert curve", Bioinformatics, 2009, pp. 1231-1235, vol. 25, No. 10.
Peter V. Kharchenko et al. "Comprehensive analysis of the chromatin landscape in *Drosophila melanogaster*", Nature, 2010, pp. 1-7.
Georgios A. Pavlopoulos et al. "Meander: visually exploring the structural variome using space-filling curves", Nucleic Acids Research, Apr. 2013, pp. 1-9, vol. 41, No. 11.
Louis Lello et al. "Accurate Genomic Prediction of Human Height", Genetics, Oct. 2018, pp. 477-497, vol. 210.
Laurens Van Der Maaten "Accelerating t-SNE using Tree-Based Algorithms", Journal of Machine Learning Research 15, 2014, pp. 3221-3245.
Yun Zhai et al. "Visual Attention Detection in Video Sequences Using Spatiotemporal Cues", ACM, Oct. 2006, pp. 815-824.
"Proceedings of the Third International Conference on Document Analysis and Recognition", Aug. 14-16, 1995, vol. 2.
Corinna Cortes et al. "Support-Vector Networks", Machine Learning, Mar. 8, 1995, pp. 273-297, vol. 20.
Emmanuel Adetiba et al. "Lung Cancer Prediction Using Neural Network Ensemble with Histogram of Oriented Gradient Genomic Features", The Scientific World Journal, 2015, pp. 1-17, vol. 2015.
Eunbyung Park et al. "Combining Multiple Sources of Knowledge in Deep CNNs for Action Recognition", 2016 IEEE Winter Conference on Applications of Computer Vision (WACV), Mar. 2016, pp. 1-8.

* cited by examiner

FIG. 5A

| Abbrev-iation | Disease/Phenotype | Abbrev-iation | Disease/Phenotype |
|---|---|---|---|
| AD | Alzheimer's disease | LM | Lipid measurements |
| AF | Atrial Fibrillation/Atrial Flutter | LOAD | Late-onset Alzheimer's disease |
| ALS | Amyotrophic Lateral Sclerosis | LONG | Longevity and age-related phenotypes |
| BA | Brain aging | MHA | Minor histocompatibility antigenicity |
| BC | Breast cancer | MI | Myocardial infarction |
| BD | Bipolar disorder | MS | Multiple sclerosis |
| BL | Blood lipids | ND | Nicotine dependence |
| BMG | Bone mass and geometry | NEU | Neuroticism |
| BPAS | Blood pressure and arterial stiffness | OBE | Obesity-related traits |
| CA | Childhood asthma | PA | Polysubstance addiction |
| CAD | Coronary Artery Disease | PC | Prostate cancer |
| CC | Colorectal cancer | PD | Parkinson's disease |
| CD | Crohn's disease | PF | Pulmonary function phenotypes |
| CDi | Celiac disease | PR | Psoriasis |

FIG. 5B

| Abbrev-iation | Disease/Phenotype | Abbrev-iation | Disease/Phenotype |
|---|---|---|---|
| CS | Coronary spasm | PSP | Progressive Supranuclear Palsy |
| CVD | Cardiovascular Disease outcomes | QT | Cardiac repolarization (QT interval) |
| EO | Early onset extreme obesity | RA | Rheumatoid Arthritis |
| GCA | General cognitive ability | RLS | Restless Leg Syndrome |
| GD | Gallstone disease | SA | Subclinical atherosclerosis |
| GLA | Glaucoma | SALS | Sporadic Amyotrophic Lateral Sclerosis |
| HAE | Hepatic adverse events with thrombin inhibitor ximelagatran | SCP | Sleep and circadian phenotypes |
| HBF | Adult fetal hemoglobin levels (HbF) by F cell levels | SLCL | Serum LDL cholesterol levels |
| HEI | Height | SLE | Systemic Lupus Erythematosus |
| HEM | Human episodic memory | SP | Schizophrenia |
| HIV1 | HIV-1 disease progression | SPBC | Sporadic post-menopausal breast cancer |
| HT | Haematological (blood) traits | SPM | Skin pigmentation |
| HYP | Hypertension | STR | Stroke |
| IC | Iris color | T1D | Type I Diabetes |
| IMAN | Immunoglobulin A nephropathy | T2D | Type II Diabetes |
| IS | Ischemic stroke | TG | Triglycerides |
| KFET | Kidney function and endocrine traits | | |

Prediction of Disease and Phenotype Association from Genome-Wide Association Studies. Stephanie et al., Plos One, 2011

FIG. 6A

| Mutation type | Example sentence |
|---|---|
| Substitution | NC_000023.10:g.33038255C>Aa substitution of the C nucleotide at g.33038255 for an A |
| Deletion | NG_012232.1:g.19del (one nucleotide) a deletion of the T at position g.19 in the sequence AGAATCACA to AGAA_CACA |
| Insertion | NC_000023.10:g.32867861_32867862insT (NM_004006.2:c.169_170insA) the insertion of an T nucleotide between nucleotides g.32867861 and g.32867861 |
| Duplication | one nucleotide - NM_004006.2:c.20dup (NC_000023.10:g.33229410dup)the duplication of a T at position c.20 in the sequence AGAAGTAGAGG to AGAAGTTAGAGG |
| Inversion | g.1077_1080invinversion of nucleotides g.1077 to g.1080, changing ..AGGCTGATT.. to ..AGGTCAGTT.. |
| Conversion | g.333_590con1844_2101conversion replacing nucleotides g.333 to g.590 with nucleotides g.1844 to g.2101 from the same genomic reference sequence |
| Repeated-sequences | reference sequences accepted are g., m., c. and n. (genomic, mitochondrial, coding DNA and non-coding DNA). |
| CNV | DNA's Regional gain or loss |
| Alleles | LRG_199t1:c.[2376G>C;3103del]one allele (chromosome) of a gene contains two different changes, g.2376G>C an c.3103del. The variants are found in cis. |

FIG. 6B

| Mutation type | Description |
|---|---|
| Substitution | a sequence change where, compared to a reference sequence, one nucleotide is replaced by one other nucleotide. |
| Deletion | a sequence change where, compared to a reference sequence, one or more nucleotides are not present (deleted). |
| Insertion | a sequence change where, compared to the reference sequence, one or more nucleotides are inserted and where the insertion is not a copy of a sequence immediately 5 |
| Duplication | a sequence change where, compared to a reference sequence, a copy of one or more nucleotides are inserted directly 3' of the original copy of that sequence. |
| Inversion | a sequence change where, compared to a reference sequence, more than one nucleotidereplacing the original sequence are the reverse complement of the original sequence |
| Conversion | a sequence change where, compared to a reference sequence, a range of nucleotides are replaced by a sequence from elsewhere in the genome |
| Repeated-sequences | a sequence where, compared to a reference sequence, a segment of one or morenucleotides (the repeat unit) is present several times, one after the othe |
| CNV | a sequence change where, compared to a reference sequence, one or more nucleotides are present(gain) and deleted(loss), and relatively longer than deletion |
| Alleles | a series of variants on one chromosome. |

FIG. 8B

(b) DNA Flanking Sequences

1, 11174426   GCAAGGGGT ⋯ AACTTCCAGCA<T>GGCCACACTG ⋯ ACGT
14, 95599770  GGGGTCATG ⋯ CTGCCATGCTG<T>GGGGTTAAGC ⋯ CTGC
22, 29095873  TCTGGTAAA ⋯ GCAGGTAGCTT<A>TTTCAGGTTATT ⋯ ATAG
21, 36171744  GACTGATCG ⋯ GTGGGGATGGT<TG>GGATCCTTG ⋯ GATC
⋮
20, 57429815  CCAGCTGCG ⋯ GGGCTCCCACT<GCC>AGCCGCTG ⋯ AGAC

(c) Protein Flanking Sequences

MTOR,  GHEFVFLLKGH ⋯ MQLFGLVNTL<L>ANDPTSLRKNLSIQR ⋯ ACGT
EPHA2, KTLKAGYTEKQ ⋯ MGQFSHHNI<I>RLEGVISKYKPMMIIT ⋯ GVISK
NRAS,  KRVKDSDDVP ⋯ LPTRTVDTKQA<H>ELAKSYGIPFIETSA ⋯ KDSD
PTEN,  ***MTAIIKEIVS ⋯ GFDLDLTYIYPNI<I>AMGFPAERLEGVYR ⋯ LDLT
⋮
CALR,  DNPEYSPDPSI ⋯ LDLWQVKSG<T>IFDNFLITNDEAYAEE ⋯ WQVK

FIG. 10B

A) Sequential
ID Tiled String

B) Sequential 2D & 3D image

Prediction of mutation biomarkers, disease-associated biomarkers and patient stratification biomarkers

FIG. 16

Degree of contribution of mutation feature information

| 5 fold validation by random sampling | | Precision | recall | f1-score |
|---|---|---|---|---|
| Features | none | 0.991832 | 0.978202 | 0.984966 |
| | driver | 0.845884 | 0.93673 | 0.888844 |
| Published driver mutations (KinDr, CanDL, IntoGen & Biomarkers) — DNA seq. | none | 0.982932 | 0.919994 | 0.948952 |
| | driver | 0.652046 | 0.870952 | 0.722652 |
| AA seq. | none | 0.986302 | 0.900492 | 0.94117 |
| | driver | 0.545556 | 0.90184 | 0.677182 |
| Hybrid (CNN+DNN) | none | 0.995406 | 0.981224 | 0.988262 |
| | driver | 0.867538 | 0.96444 | 0.913366 |

FIG. 19 data set: odd_ratio_a; accuracy: 0.86; confusion_matrix [[19 16] [ 0 84]]

|  | precision | recall | f1-score | support |
|---|---|---|---|---|
| normal | 1.00000 | 0.54286 | 0.70370 | 35 |
| pd | 0.84000 | 1.00000 | 0.91304 | 84 |
| avg/total | 0.88706 | 0.86555 | 0.85147 | 119 |

$$OR\_a = \frac{(N12*1+N22*1) \text{ disease}}{(N12*1+N22*1) \text{ normal}}$$

data set: odd_ratio_b; accuracy: 0.92; confusion_matrix [[29 6] [ 3 81]]

|  | precision | recall | f1-score | support |
|---|---|---|---|---|
| normal | 0.90625 | 0.82857 | 0.86567 | 35 |
| pd | 0.93103 | 0.96429 | 0.94737 | 84 |
| avg/total | 0.92374 | 0.92437 | 0.92334 | 119 |

$$OR\_b = \frac{(N12*1+N22*2) \text{ disease}}{(N12*1+N22*2) \text{ normal}}$$

data set: odd_ratio_c; accuracy: 0.87; confusion_matrix [[23 12] [ 3 81]]

|  | precision | recall | f1-score | support |
|---|---|---|---|---|
| normal | 0.88462 | 0.65714 | 0.75410 | 35 |
| pd | 0.87097 | 0.96429 | 0.91525 | 84 |
| avg/total | 0.87498 | 0.87395 | 0.86786 | 119 |

$$OR\_c = \frac{(N12) \text{ disease}}{(N12) \text{ normal}}$$

*OR (a, b & c) were calculated with normalized case (Parkinson's patient group) and control (normal group)

HILBERT-CNN: AI-DRIVEN CONVOLUTIONAL NEURAL NETWORKS WITH CONVERSION DATA OF GENOME FOR BIOMARKER DISCOVERY

CROSS REFERENCE TO PRIOR APPLICATIONS

This application claims priority to and the benefit of Korean Patent Application Nos. 10-2017-0123731 filed on Sep. 25, 2017 and 10-2017-0185041 filed on Dec. 31, 2017, the disclosure of which are incorporated herein by reference in their entirety.

BACKGROUND

The present invention relates to a method and a system for detecting biomarkers using an artificial intelligence (AI) deep learning model. The method and system according to the present invention have been developed in consideration of interactions between various population genome sequences and mutations in widely distributed next-generation sequencing environments, and comprise converting nucleotide sequences including mutations into conversion data in a one-dimensional string, two-dimensional image or three-dimensional cubic form, and analyzing the correlation of the conversion data with clinical information (diseases or phenotypes).

Single polymorphism information (SNP), insertion/deletion (INDEL) and structural variation (SV), which account for more than 0.1% of the human genome sequence, have been the subject of linking human clinical information with phenotypes. Accordingly, various platforms have been studied to perform accurate and rapid analysis, identify genetic biomarkers suitable for clinical information, and stratify patients layering patients.

In particular, currently, due to gene-gene interactions and mathematical and statistical limitations in the field of disease association research, research is effectively conducted only specific SNP regions based on GWAS (genome-wide association study) which is the major field of disease association research.

Furthermore, the accuracy of driver mutation detection and patient stratification research results increases as more human genome data is collected. Up to now, only for chip data on specific SNP regions, data have been secured to such an extent that the reliability can be ensured. However, for the whole genome sequence, there has been much difficulty in optimizing data size and operation for integration and analysis.

A brief description of general procedures of driver mutation detection, disease association studies and patient stratification studies is as follows.

Genome sequencing data are generated from samples (blood, paraffin blocks, or cell-free DNA) to be tested, and a nucleotide format file is generated by extracting specific regions to be tested.

However, storing and extracting many various mutations of many people in the form of nucleotide sequences while maintaining the sequence of three billion nucleotides was almost impossible in time.

So, multiple alignment maps which are partially consistent are made in order to conduct disease association studies and GWAS (genome-wide association study).

For this reason, it is practically impossible to apply GWAS to nucleotide insertion/deletion (indel), long nucleotide variation (structural variation), variation in one strand among two diploid strands (copy number variation), and small but significant or large structural variation, and even if it is possible, the efficiency is lowered and a lot of genomic data are left untouched.

In addition, when the prior art was used in order to overcome such problems, statistics based on common cumulative information on a locus or loci with minor allele frequency >0.01 based on tens or hundreds of thousands of genomic data were the only alternatives. In this case, there were problems, including large-scale population genome projects, long time and high costs, complicated analyzes and procedures, and low or reduced efficiency with which only a portion is analyzed.

In particular, as genome studies have further been conducted, the importance of gene-gene interactions has emerged. Because complex diseases are not diseases based on one mutation, but are diseases caused by complex relationships based on multiple mutations in multiple genes, it was faced with the difficulty of analyzing multiple mutations.

Meanwhile, since Google recently released Tensorflow-based deep learning technology as an open source, many bioinformatics algorithms have changed very quickly into Google's Tensorflow-based deep learning, and many bioinformatics programs already changed into deep learning.

In addition, innovation in Google Tensorflow-based deep learning continues such that deep learning is positioned at the top of information innovation network.

Furthermore, currently, one of the key elements of innovation in Google's Tensorflow-based deep learning technology is the calculation of a 3D plane, which is made possible by an mVIDIA graphic card (GPGPU; general purpose process unit).

In addition, the Volta version of GPGPU has recently released, which includes 30,000 cores and is accelerating the development of Tensorflow deep learning technology. As such, the analytical technology using the graphic card is exponentially faster, but it was difficult to program. However, currently, this technology makes it easy for anyone to load Tensorflow into a library in a Python environment and make necessary calculations.

Thanks to the rapid development of this IT field, Tensorflow-based deep learning has given many innovative results, particularly, to the image search area. As one of these results, when the work of Vincent Willem van Gogh is learned and a completely different picture is provided as an input, pictures similar to the work of van Gogh are drawn. This was demonstrated in Google Cloud as shown in FIG. 1.

In addition, thanks to the above-described next generation sequencing technology, studies have been reported in which methods of detecting driver mutation biomarkers, disease-associated biomarkers and patient stratification biomarkers in whole genome sequencing and target sequencing are applied to the sequence of three billion nucleotides or target genes of the human genome.

However, it can be seen that recent algorithms for detecting these mutation-based biomarkers [see Non-Patent Documents 1 to 23 below] are far from deep learning which is performed by converting genomes into 2D or 3D-based data.

In particular, in Non-Patent Documents 24 to 26, deep learning-based techniques of analyzing motifs by using the nucleotide sequences of human genome sequencing data in epigenomic regions have appeared.

However, these techniques merely assign simple sequence motifs and about 1,000 bases to one pixel and analyze the structural variation (translocation, fusion, etc.) of the genome.

Meanwhile, regarding data conversion technology, Patent Documents 1 to 3 below disclose a method of converting continuous numbers and sequence information into 2D images by the Hilbert space-filling method as shown in FIG. 2.

The Hilbert space-filling curve which has been buried for a long period of time since constructed by the algebraists Hilbert & Peano in 1890s has demonstrated its usefulness and utility since 2001, when computer systems have been improved dramatically. In 2001, Jonathan (the University of London) first filed a patent application relating to "a method of storing and extracting data using the Hilbert theory" in the United States.

Next, U.S. Pat. No. 7,454,055, a patent relating to data compression, was issued in 2008.

Meanwhile, in the biological area, as described in Non-Patent Documents 26 to 28, a paper relating to two-dimensional imaging of methylation in genomic information was published by Simon. Then, in 2011, Nature published a paper relating to two-dimensional visualization of an epigenome based on methylation of the drosophila genome.

In addition, Zuguang (China) published "a method of two-dimensional imaging of copy number variation based on the start position and end position of genomic copy number variation" in a bioinformatics paper in 2016, and obtained allowance of "a method of storing and extracting a DB by a method different from Lawder" in 2017.

However, when the above-described method of nucleotide sequence information (such as consecutive numbers) into a two-dimensional image by the Hilbert space-filling method is applied to the sequence of three billion nucleotides in order to predict and detect disease-associated biomarkers, the following problems arise.

That is, in the prior art as described above, visualization of epigenomic methylation of the drosophila genome as described by Simon in 2011, detection of structural variation as described by Pavlopoulos, and limitations of CNV (copy number variation) as described by Zuguang in 2016, correspond to the application of the start position and end position of nucleotide sequences, which need to be visualized, to the Hilbert curve.

Therefore, eukaryotes having diploid characteristics, like the human genome, have two pairs of nucleotide sequences, and hence have SNP (single nucleotide polymorphism) and INDEL (insertion and deletion) genotypes (AA, AB or BB; homozygote, heterozygote or alternative homozygote). However, in the prior art, there was a limitation in that it was impossible to generate and analyze conversion data to which diploids for analysis of driver mutation markers, disease-associated biomarkers and patient stratification biomarkers were applied in consideration of the characteristics of such diploids.

Meanwhile, Non-Patent Document 30 is the only paper that describes a technique of predicting height based on machine learning by use of 600,000 mutations of the human genome, but it can be seen that this technique is different from deep learning based on conversion data.

Thus, studies on the detection of driver mutation biomarkers, disease-associated biomarkers and patient stratification biomarkers in whole genome sequencing and target sequencing according to the prior art had a problem in that it is difficult to accurately check problems caused by highly polymorphic regions of human genes, linkage disequilibrium (LD), structural variation, gene sequence duplication, gene-gene interactions, and spatial interactions.

Meanwhile, the following non-patent prior art documents are classified as follows according to their main contents.

Documents 1 to 23 are papers related to predicting biomarkers based on mutation features;

Documents 24 to 25 are papers related to deep machine learning for regulation and prediction of expression;

Documents 26 to 29 are papers related to algorithms for detecting methylation, CNV and SV based on the Hilbert curve;

Document 30 is a paper related to calculating the height of the human genome by machine learning; and Documents 31 to 34 are papers related to t-SNE, Saliency map, RF (Random Forest), and SVM (Support Vector Machine), which are data classifiers.

PRIOR ART DOCUMENTS

Patent Documents (Patent Document 1) U.S. Pat. No. 7,167,856 B1 (Lawder et al.).

(Patent Document 2) US 20110150140 A1 (Alexopoulos et al.).

(Patent Document 3) U.S. Pat. No. 7,245,196 B1 (Baliarda et al.).

Non-Patent Documents (Non-Patent Document 1) SIFT: Kumar, Prateek, Steven Henikoff, and Pauline C. Ng. "Predicting the effects of coding non-synonymous variants on protein function using the SIFT algorithm." Nature protocols 4.7 (2009): 1073-1081.

(Non-Patent Document 2) Polyphen-2: I. A. Adzhubei, S. Schmidt, L. Peshkin et al., method and server for predicting damaging missense mutations, Nature Methods, vol. 7, no. 4, pp. 248249, 2010.

(Non-Patent Document 3) LRT S. Chun and J. C. Fay, of deleterious mutations within three human genomes, Genome Research, vol. 19, no. 9, pp. 15531561, 2009.

(Non-Patent Document 4) Polyphen-2 HDIV n HDVAR Score: Yunos, R. I. M., Ab Mutalib, N. S., Khor, S. S., Saidin, S., Nadzir, N. M., Razak, Z. A., & Jamal, R. (2016). Characterisation of genomic alterations in proximal and distal colorectal cancer patients (No. e2109v1). PeerJ Preprints.

(Non-Patent Document 5) MutationAccessor1: Reva, B., Antipin, Y., & Sander, C. (2011). Predicting the functional impact of protein mutations: application to cancer genomics. Nucleic acids research, 39(17), e118-e118.

(Non-Patent Document 6) MutationAccessor2: Gnad, F., Baucom, A., Mukhyala, K., Manning, G., & Zhang, Z. (2013). Assessment of computational methods for predicting the effects of missense mutations in human cancers. BMC genomics, 14(3), S7.

(Non-Patent Document 7) MUTATIONTASTER: Dong, C., Wei, P., Jian, X., Gibbs, R., Boerwinkle, E., Wang, K., & Liu, X. (2014). Comparison and integration of deleteriousness prediction methods for nonsynonymous SNVs in whole exome sequencing studies. Human molecular genetics, 24(8), 2125-2137.

(Non-Patent Document 8) Mutation Accessor and Mutation Taster: Oishi, Maho, et al. "Comprehensive Molecular Diagnosis of a Large Cohort of Japanese Retinitis Pigmentosa and Usher Syndrome Patients by Next-Generation Sequencing Diagnosis of RP and Usher Syndrome Patients by NGS." Investigative ophthalmology & visual science 55.11 (2014): 7369-7375.

(Non-Patent Document 9) PhyloP46way_placental and PhyloP46way_vertebrate: Pollard, Katherine S., et al. "Detection of nonneutral substitution rates on mammalian phylogenies." Genome research 20.1 (2010): 110-121.

(Non-Patent Document 10) GERP++_RS Score: Davydov, E. V., Goode, D. L., Sirota, M., Cooper, G. M., Sidow, A., & Batzoglou, S. (2010). Identifying a high fraction of the human genome to be under selective constraint using GERP++. PLoS computational biology, 6(12), e1001025.

(Non-Patent Document 11) B62 Score: Tsuda, H., Kurosumi, M., Umemura, S., Yamamoto, S., Kobayashi, T., & Osamura, R. Y. (2010). HER2 testing on core needle biopsy specimens from primary breast cancers: interobserver reproducibility and concordance with surgically resected specimens. BMC cancer, 10(1), 534.

(Non-Patent Document 12) Siphy: Garber, Manuel, et al. "Identifying novel constrained elements by exploiting biased substitution patterns." Bioinformatics 25.12 (2009): i54-i62.

(Non-Patent Document 13) CHASM: H. Carter, J. Samayoa, R. H. Hruban, and R. Karchin, of driver mutations in pancreatic cancer using cancerspecific high-throughput annotation of somatic mutations (CHASM), Cancer Biology & Therapy, vol. 10, no. 6, pp. 582587, 2010.

(Non-Patent Document 14) Dendrix: F. Vandin, E. Upfal, and B. J. Raphael, novo discovery of mutated driver pathways in cancer, Genome Research, vol. 22, no. 2, pp. 375385, 2012.

(Non-Patent Document 15) Mutsig CV: M. S. Lawrence, P. Stojanov, P. Polak et al., heterogeneity in cancer and the search for new cancer-associated genes, Nature, vol. 499, no. 7457, pp. 214218, 2013. [68] M. Kanehisa and S. Goto, kyoto encyclopedia.

(Non-Patent Document 16) FATHMM: Shihab, Hashem A., et al. "Predicting the functional, molecular, and phenotypic consequences of amino acid substitutions using hidden Markov models." Human mutation 34.1 (2012): 57-65.

(Non-Patent Document 17) VEST3_score: Carter, Hannah, et al. "Identifying Mendelian disease genes with the variant effect scoring tool." BMC genomics 14.3 (2013): S3.

(Non-Patent Document 18) MetaSVM: Nono, Djotsa, et al. "Computational Prediction of Genetic Drivers in Cancer." eLS (2016).

(Non-Patent Document 19) MetaLR: Dong, Chengliang, et al. "Comparison and integration of deleteriousness prediction methods for nonsynonymous SNVs in whole exome sequencing studies." Human molecular genetics 24.8 (2014): 2125-2137.

(Non-Patent Document 20) CADD: Kircher, Martin, et al. "A general framework for estimating the relative pathogenicity of human genetic variants." Nature genetics 46.3 (2014): 310-315.

(Non-Patent Document 21) CADD 2: Velde, K. Joeri, et al. "Evaluation of CADD scores in curated mismatch repair gene variants yields a model for clinical validation and prioritization." Human mutation 36.7 (2015): 712-719.

(Non-Patent Document 22) CADD 3: Mather, Cheryl A., et al. "CADD score has limited clinical validity for the identification of pathogenic variants in non-coding regions in a hereditary cancer panel." Genetics in medicine: official journal of the American College of Medical Genetics (2016).

(Non-Patent Document 23) ParsSNP: Kumar, Runjun D., S. Joshua Swamidass, and Ron Bose. "Unsupervised detection of cancer driver mutations with parsimony-guided learning." Nature genetics 48.10 (2016): 1288-1294.

(Non-Patent Document 24) Deep machine learning for regulation and prediction of expression; DeepCpG: accurate prediction of single-cell DNA methylation states using deep learning. Christof et al., Genome Biologym 2017m 18:67.

(Non-Patent Document 25) Deep machine learning for regulation and prediction of expression: SpliceVec: distributed feature representations for splice junction prediction. Aparajita Dutta et al., Biorxiv, 2018, https://doi.org/10.1101/183087 (Non-Patent Document 26) 2D visualization of 1D genome: Gu Z, Eils R and Schlesner M (2016). an R/Bioconductor package for high-resolution visualization of genomic data.

(Non-Patent Document 27) 2D visualization of 1D genome: Anders Simon (2009). of genomic data with the Hilbert curve.

(Non-Patent Document 28) Visualization of 1D nucleotide sequence of drosophila genome by Hilbert imaging: Kharchenko et al., Comprehensive analysis of the chromatin landscape in *Drosophila melanogaster*. Nature. 2011 Mar. 24; 471(7339):480-5. doi: 10.1038/nature09725. Epub 2010 Dec. 22.

(Non-Patent Document 29) Detection of structural variation based on Hilbert images: Pavlopoulos et al., Meander: visually exploring the structural variome using space-filling curves. Nucleic Acids Res. 2013.

(Non-Patent Document 30) Machine learning for genomic patient stratification: Louis Lello et al., Accurate Genomic Prediction Of Human Height. bioRxiv, 2018.

(Non-Patent Document 31) Tree-based algorithm (t-SNE): Louis Lello et al., Accelerating t-SNE using Tree-Based Algorithms. Journal of Machine Learning Research, 15:3221-3245, 2014.

(Non-Patent Document 32) Saliency map: Zhai et al., Visual Attention Detection in Video Sequences Using Spatiotemporal Cues.

Proceedings of the 14th ACM International Conference on Multimedia, MM '06. New York, NY, USA: ACM: 815824.

(Non-Patent Document 33) Random Forests (RF): Tin Kam et al., Proceedings of the 3rd International Conference on Document Analysis and Recognition, Montreal, QC. 1416 August 1995. pp. 278282.

(Non-Patent Document 34) Support Vector Machine (SVM): Cortes et al., Support-vector networks. Machine Learning. 20 (3): 273297.

SUMMARY

The present invention has been made in order to solve the above-described problems occurring in the prior art, and is intended to provide a method of detecting driver mutation biomarkers, disease-associated biomarkers and patient stratification biomarkers by use of data converted into a one dimensional string, two-dimensional image or three-dimensional cubic form in view of the features of multiple genome sequences and mutations in next generation sequencing, diploid information, and gene-gene interactions, and by use of clinical information (diseases or phenotypes), wherein the method is a method of detecting biomarkers using artificial intelligence (AI) deep learning for conversion data of multiple genome sequences and mutations and has significantly improved accuracy and efficiency due to a step of performing learning through an AI deep learning model.

Specifically, the present invention is intended to a method and a system of disease-associated biomarkers and patient stratification biomarkers in the genomes of different samples using multiple genome sequences, 1D flanking sequences, 2D images, Hilbert curves and Fractal curves by the use of: 1) a method of ensuring the whole genome sequence or target sequence length; 2) a method of expressing various mutation types reflecting the characteristics of diploids; 3) a method of using the feature or pattern of mutations at each locus of each nucleotide sequence, and making one-dimensional strings (franking sequences) reflecting 1) to 3); 4) a method of using clinical information and phenotypes; 5) a method of allowing an AI deep learning model to learn the detection of driver mutation biomarkers, disease-associated biomarkers and biomarkers for patient stratification research by use of CNN (convolutional neural network), DNN (deep neural network), or a hybrid thereof; and 6) a method of using Tsne (Non-Patent Document 31), Saliancy map (Non-Patent Document 32), RF (Non-Patent Document 33), SVM (Non-Patent Document 34) and the like, which are classifiers based on deep learning and classified information.

To achieve the above object, the present invention provides a method for detecting biomarkers, comprising the steps of: (A) collecting nucleotide sequences and mutations of population genomes; (B) generating conversion data by reflecting mutations of diploid genomes in the collected nucleotide sequences; (C) performing an artificial intelligence (AI) deep learning model with the generated conversion data; (D) generating a fully connected network (FCN) by connecting the results obtained by the machine learning; and (E) extracting biomarkers by the learned model.

Here, the population may be classified according to the type of disease or according to the class of responder patients.

Furthermore, the collecting of the nucleotide sequences and mutations of population genomes in step (A) comprises generating the nucleotide sequences of the genomes from next-generation sequencing data on the basis of GATK best-practice or a similar method; and the generating of the nucleotide sequences on the basis of the GATK best-practice comprises generating the nucleotide sequences in the form of FASTQ BAM (binary alignment map) or VCF (variant allele format).

In addition, the biomarkers may be driver mutations (cancer/rare disease mutations), and the generating of the conversion data in step (B) may comprise the steps of: (B1-1) generating one-dimensional strings (flanking sequences) composed of nucleotides of all population samples; and (B1-2) calculating the features of mutations positioned in the center of each of the one-dimensional strings. In addition, the biomarkers may be biomarkers for stratification of responder patients and disease-associated biomarkers, and the generating of the conversion data in step (B) may comprise the steps of: (B2-1) generating a master template which is a locus template of unique mutations, which consists of an union of the nucleotide sequence mutations of the population genomes; (B2-2) generating conversion data by converting the mutations of the master template and the population genomes into a set of unit data expressed as feature information; (B2-3) selecting risk or protective allele mutations; (B2-4) making two-dimensional images of nucleotide sequences or mutations, which have a 2D image size (32 pixels*32 pixels=1,024 mutations, 64*64=4,096 mutations, 128*128=16,384 mutations, 256*256=65,536 mutations, 512*512=263,680 mutations, 1024*1024=1,048,576 mutations, etc.), from the whole of the risk and protective allele mutations, or the risk allele mutations and the protective allele mutations in the same number, or only the risk allele mutations; and (B2-5) filtering whether or not the biomarkers selected in step (B2-4) above are present in public mutation data for use as biomarkers.

The integrated form of the population is expressed in a matrix form as follows:

X-axis: composed of locus position coordinates of each sample of the population;

Y-axis: the population is composed of two groups (i.e., patient 1, patient 2, . . . patient N, normal 1, normal 2, . . . normal M);

N+M=total number of patients, N: number of normal people, M: number of patients;

NN11: number of homozygotes counted at each locus of normal people;

NN12: number of heterozygotes counted at each locus of normal people;

NN13: number of alternative homozygotes counted at each locus of normal people;

DN11: number of homozygotes counted at each locus of patients;

DN12: number of heterozygotes counted at each locus of patients;

DN13: number of alternative homozygotes counted at each locus of patients;

Risk Odds ratio=([$DN12+DN13*2$]/$M$)/([$NN12+NN13*2$]/$N$);

Protective Odds ratio=([$NN12+NN13*2$]/$N$)/([$DN12+DN13*2$]/$M$).

For convenience, among the counted values of homozygotes and alternative homozygotes, the greater value is defined as homozygotes, and the smaller value is defined as alternative homozygotes. In addition, if the number of samples is small, using all three billion nucleotides will result in an image that is excessively large. For this reason, when a 2D Hilbert form (Fractal or three-dimensional cubic form) is generated only with highly risky or highly protective mutations by use of using the above-described odd ratio, the efficiency increases. In other words, the mutations are selected in descending order of risk alleles, and the mutations are selected in descending order of the odds ratio of protective alleles. In addition, when the selected mutations are present in the public mutation data, prevalence information and minor allele frequency information can be used based on the public mutation data. Therefore, filtering the genome mutations based on whether or not the mutations are present in the public mutation data is essential for the use of biomarkers.

Therefore, feature information on mutation biomarkers and the risk allele mutations or the protective allele mutations can be expressed as the color of unit data (pixel), characters, or a combination thereof.

In addition, the conversion data may be data converted into a one-dimensional string, two-dimensional image or three-dimensional cubic form.

The conversion data in the one-dimensional string form may be generated by arranging the unit data according to the nucleotide sequence.

The conversion data in the two-dimensional image form may be generated by arranging the conversion data of the one-dimensional string form into a two-dimensional image form by the Hilbert-curve method.

The conversion data in the three-dimensional cubic form can be generated by sequentially arranging the conversion data of the two-dimensional image form into the three-dimensional cubic form.

The conversion data in the two-dimensional image form may be generated by arranging the conversion data of the one-dimensional string form into a two-dimensional image form by the Fractal-curve method.

The conversion data in the three-dimensional cubic form may be generated by sequentially arranging the conversion data of the two-dimensional image form into the three-dimensional cubic form.

Furthermore, the artificial intelligence (AI) learning model in step (C) may be performed by comparing the conversion data of the mutations of each population genome based on the conversion of the master template.

In addition, the master template may be generated with valid mutations selected from among the mutations of the population genomes according to the degree of redundancy.

In addition, the artificial intelligence (AI) learning model in step (C) may be configured to learn mutations of the master template with mutations of the population genomes by two or more algorithms of Convolutional Neural Network (CNN), Deep Neural Network (DNN) and Recurrent Neural Network (RNN).

In addition, the method comprises the steps of: (D) generating a fully connected network (FCN) by connecting the results obtained by the machine learning; and (E) extracting biomarkers by the learned model.

In addition, the biomarkers may be genetic mutation biomarkers associated with diseases.

In addition, the biomarkers may be biomarkers that are involved in patient stratification.

In addition, the method of the present invention may further comprise a step of verifying the extracted biomarkers using known biomarkers.

BRIEF DESCRIPTION OF THE DRAWINGS

FIG. 5 illustrates an example of clinical information and phenotypes on a control group according to a specific embodiment of the present invention.

FIG. 6 is a table showing an example of diploid mutation types of a control group according to a specific embodiment of the present invention. FIG. 6 contains the following SEQ IDs:

SEQ ID 17: AGAAGTAGAGG

SEQ ID 18: AGAAGTTAGAGG

Figure 7:
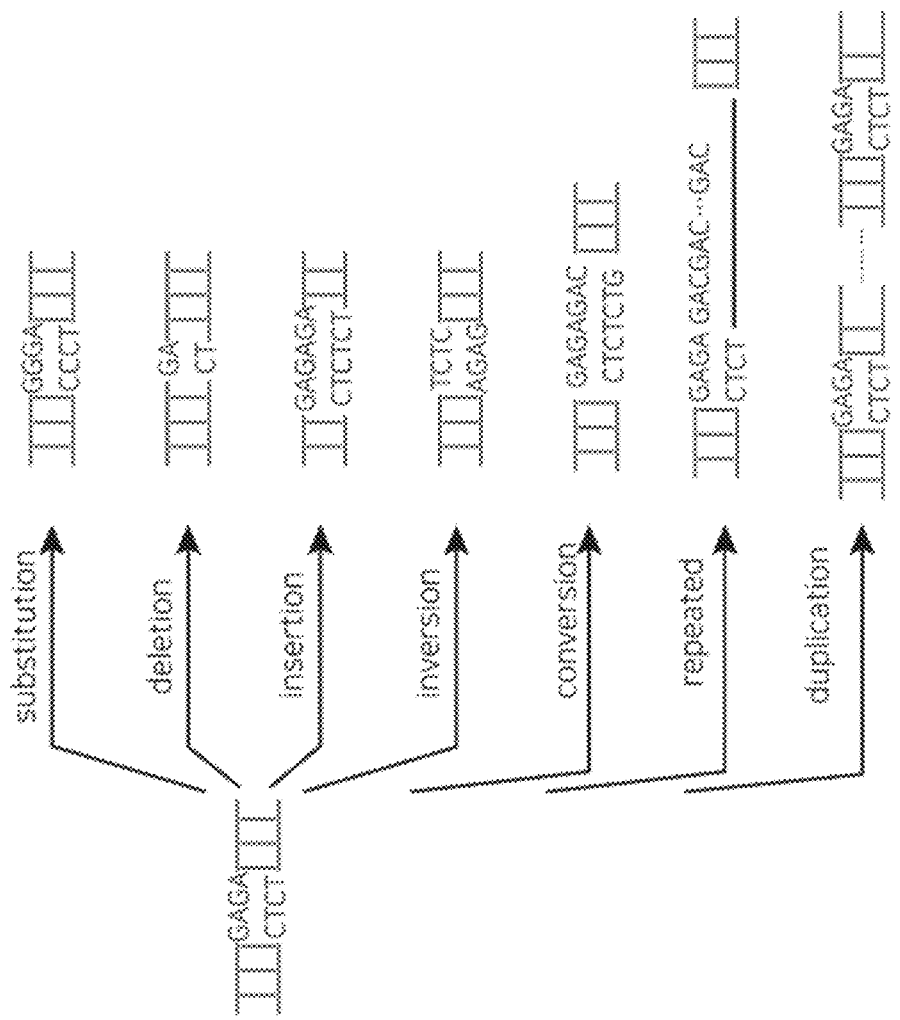

FIG. 7 schematically illustrates an example of diploid mutation types of a control group according to a specific embodiment of the present invention.

FIG. 8 illustrates the mutation feature types and 1D strings of conversion data according to a specific embodiment of the present invention. FIG. 8 contains the following SEQ IDs:

```
SEQ ID 2:
GCAAGGGGT . . . AACTTCCAGCA<T>GGCCACACTG . . . ACGT

SEQ ID 3:
GGGGTCATG . . . CTGCCATGCTG<T>GGGGTTAAGC . . . CTGC

SEQ ID 4:
TCTGGTAAA . . . GCAGGTAGCTT<T>TTTCAGGTTATT . . . ATAG

SEQ ID 5:
GACTGATCG . . . GTGGGGATGGT<TG>GGATCCTTG . . . GATC

SEQ ID 6:
CCAGCTGCG . . . GGGCTCCCACT<GCC>AGCCGCTG . . . AGAC

SEQ ID 7:
GHEFVFLLKGH . . . MQLFGLVNTL<L>ANDPTSLRKNLSIQR . . . ACGT

SEQ ID 8:
KTLKAGYTEKQ . . . MGQFSHHNI<I>RLEGVISKYKPMMIIT . . . GVISK

SEQ ID 9:
KRVKDSDDVP . . . LPTRTVDTKQA<H>ELAKSYGIPFIETSA . . . KDSD

SEQ ID 10:
* * * MTAIIKEIVS . . . GFDLDLTYIYPNI<I>AMGFPAERLEGVYR . . . LDLT

SEQ ID 11:
DNPEYSPDPSI . . . LDLWQVKSG<T>IFDNFLITNDEAYAEE . . . WQVK
```

Figure 9:
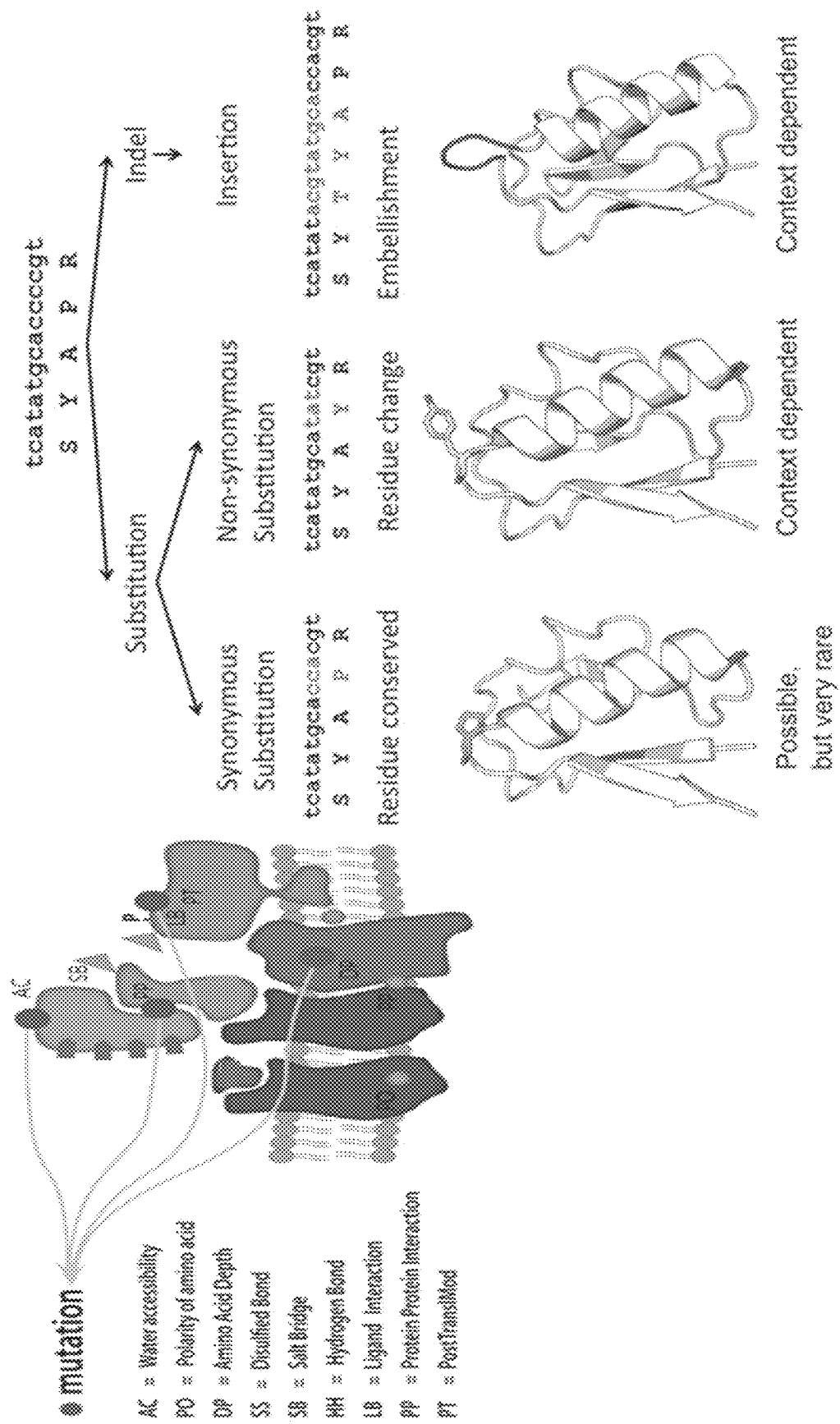

FIG. 9 illustrates 3D structure profiles among the mutation feature types of conversion data according to a specific embodiment of the present invention. FIG. 9 contains the following SEQ IDs:

SEQ ID 12:
tcatatgcaccccgt

SEQ ID 13:
tcatatgcaccacgt

SEQ ID 14:
tcatatgcatatcgt

SEQ ID 15:
tcatatacgtatgcaccacgt

Figure 10A:
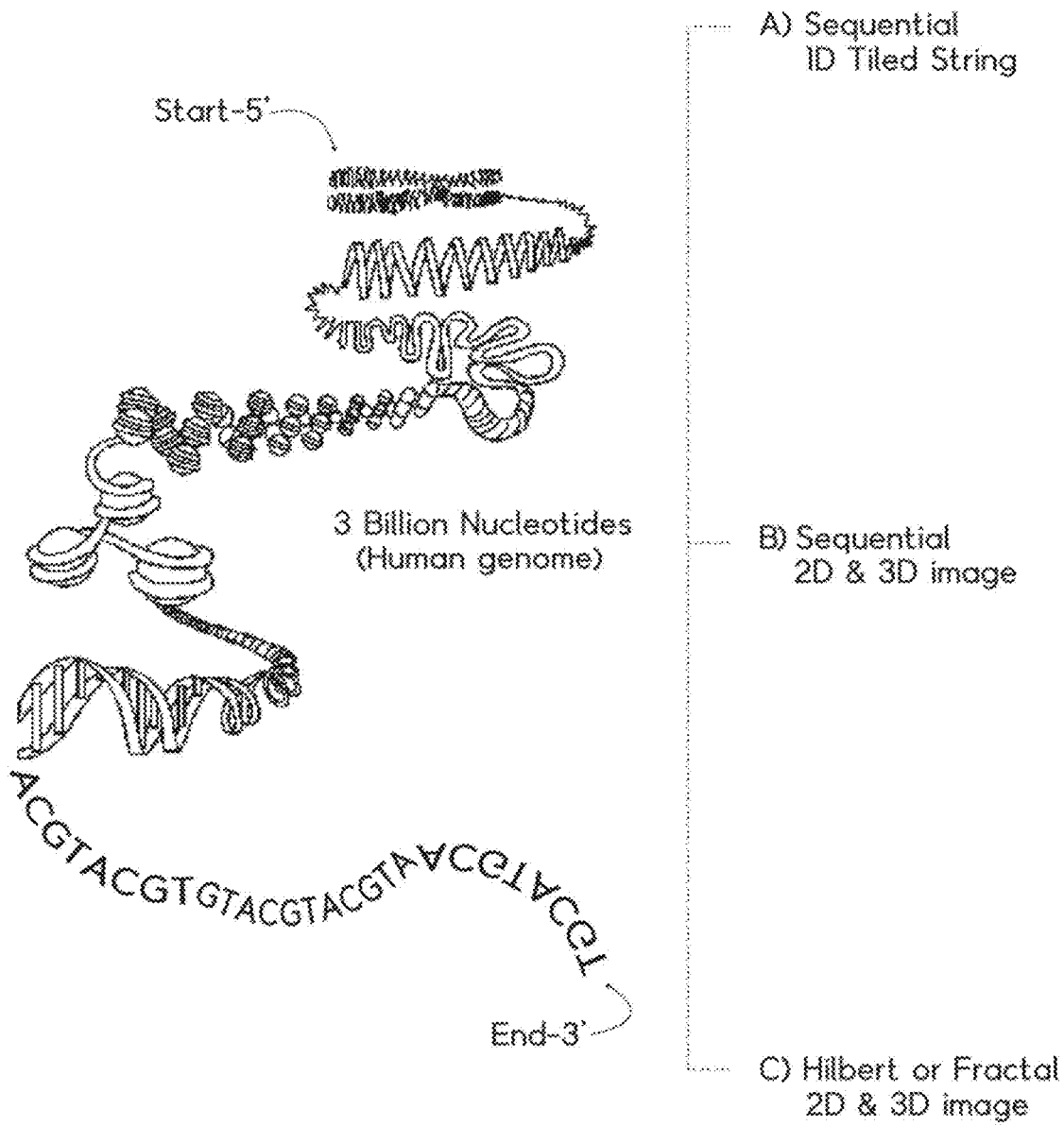
Figure 10B:
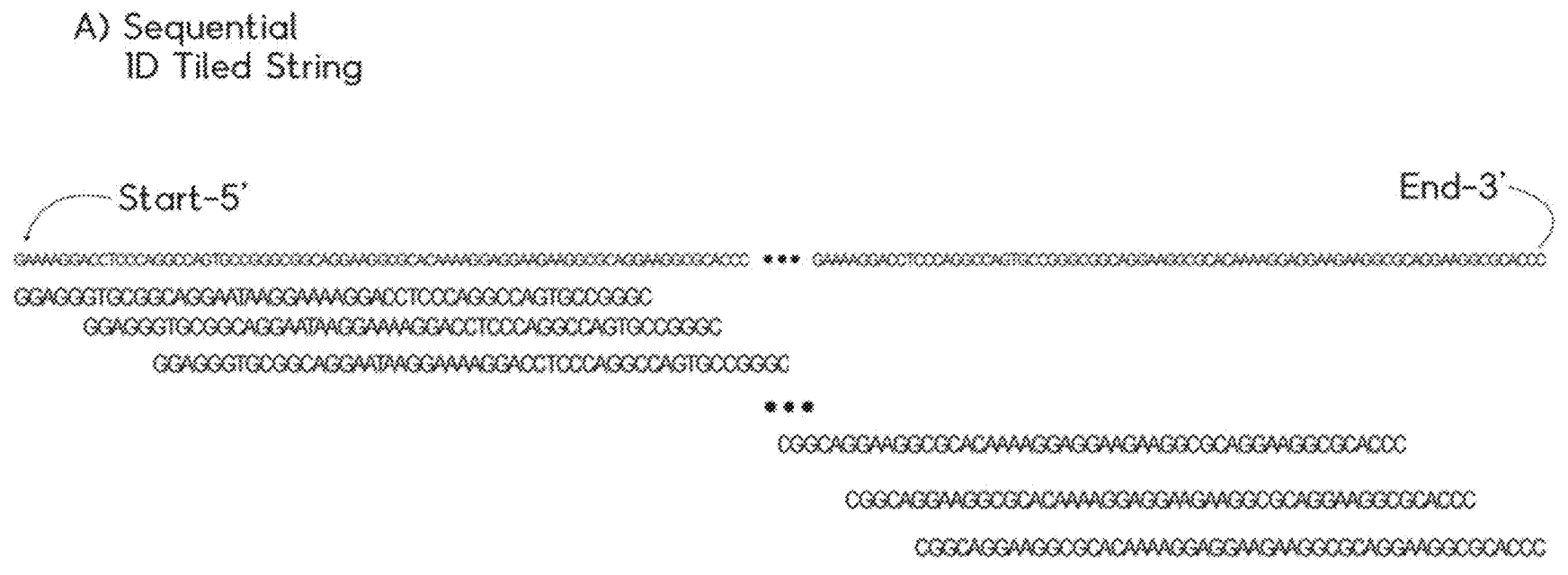
Figure 10C:
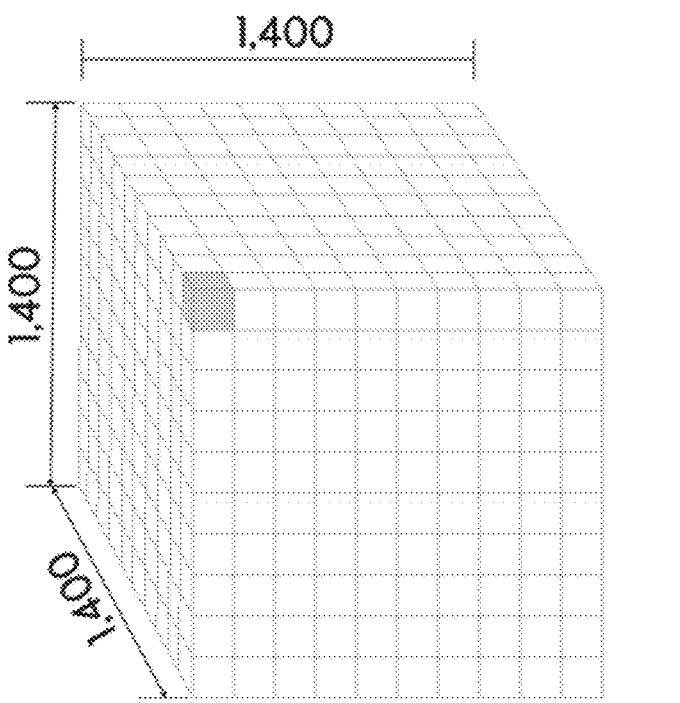
Figure 10D:
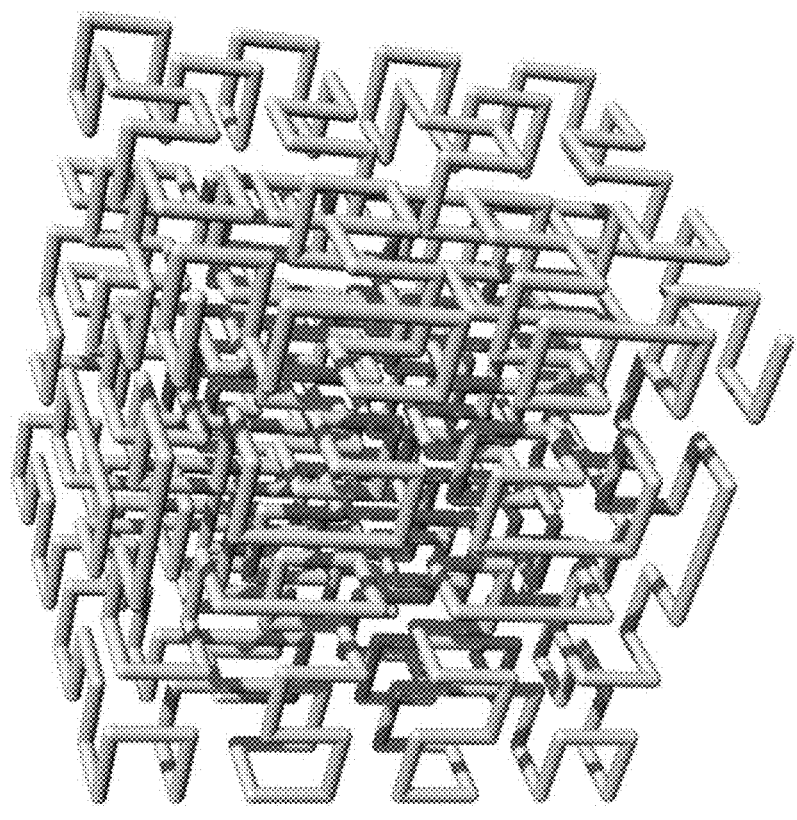

FIG. 10 illustrates an example of converting data into higher-dimensional images according to a specific embodiment of the present invention. FIG. 10 contains the following SEQ IDs: IDC-23 DNA M

SEQ ID 16:
ACGTACGTGTACGTACGTAACGTACGT

SEQ ID 19:
GAAAAGGACCTCCCAGGCCAGTGCCGGGCGGCAGGAAGGCGCACAAAAGG

AGGAAGAAGGCGCAGGAAGGCGCACCC . . . GAAAAGGACCTCCCAG

GCCAGTGCCGGGCGGCAGGAAGGCGCACAAAAGGAGGAAGAAGGCGCAGG

AAGGCGCACCC

SEQ ID 20:
CCATTGTCCCCCGGCCTCCTCTGCCCTGCCCCTGGAGGGTGCGGCAGGAA

TAAGGAAAAGGACCTCCCAGGCCAGTGCCGGGCGGCAGGAAGGCGCACCC

AGGAACTTCTTCTGGAAGACCGCAAGTTTAATTACAGACC

SEQ ID 21:
GCTGCTGCTGCTCTCCGGGGCCACCGGCCGAGACAGCGAGCTCCTGACTT

TCCTCGCTTGCCTCATAGGAGAGGAAGCTCAGCAATCCGCGCGCCGGGAC

TCCTCCTGCAAATAAAACCTCACCACCGACAAGCCAGGCGAGAATGCC

SEQ ID 22:
AGGAACTTCTTCTGGAAGACGCGGCAGGAAGGCGCACCCGACCTCCCAG

GCCAGTGCCGGCGGCAGGAATAAGGAAAAGCTGCCCTGCCCCTGGAGGGT

GATGCCATTGTCCCCCGGCCGGCGGCAGGAAGGCGCACCC

SEQ ID 23:
TCCTCCTGCAAATAAAACCTCACCAGCAATCCGCGCGCCGGGACCCTCAT

AGGAGAGGAAGCTCCTCCTGACTTTCCTCGCTTGCCACCGGCCGAGACAG

CATAGCTGCTGCTGCTCTCCGGGGGCGGCAGGAAGGCGCACCC

SEQ ID 24:
GAGCAAAGACACAAAGACCGCCATTGTCCACACATGATAGGTGAGACAAA

GCGTTAGAGC

SEQ ID 25:
GTCAACAGACGCAAAGAGTGAAAGGTTCCACGTGTACATAGTGCGACAGA

ACGACCCACG

SEQ ID 26:
TACACACAACGTACAAGGTGCATGACAAAATGCGCCAGTGCATGCGAGGA

TAAAGCACAAGGTG

SEQ ID 27:
GATGACAAACGTGTGGAACAAATGCACAACAAACGCATTGGTGCGTCAGA

TACACAACCGCGTG

Figure 11:
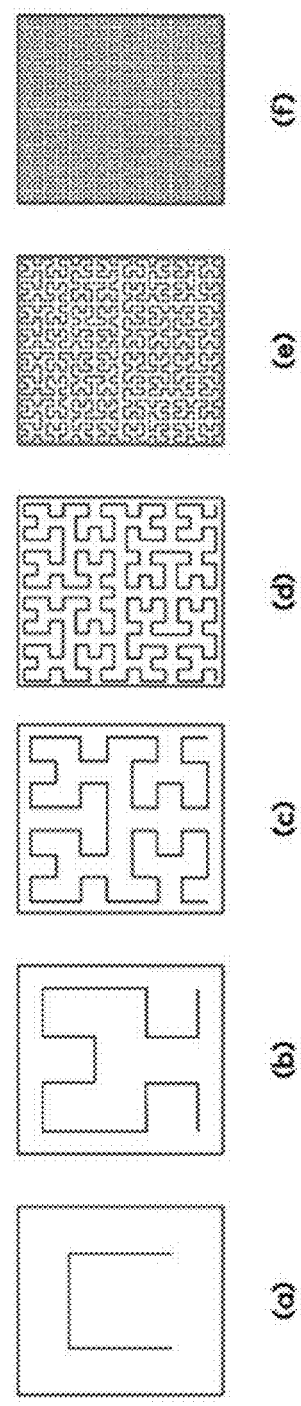

FIG. 11 illustrates an example of generating the Hilbert curve according to a specific embodiment of the present invention.

Figure 12:
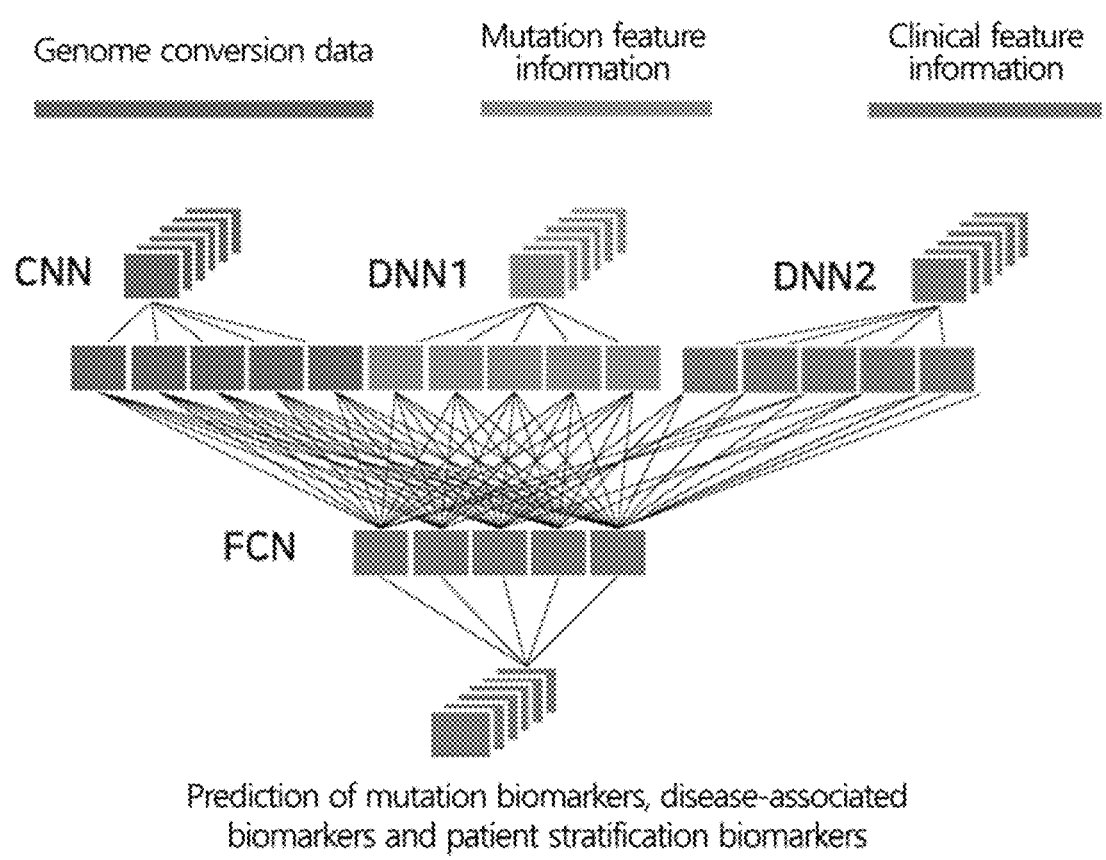

FIG. 12 illustrates a process of separating and combining CNN and DNN in a deep learning process according to a specific embodiment of the present invention.

Figure 13:
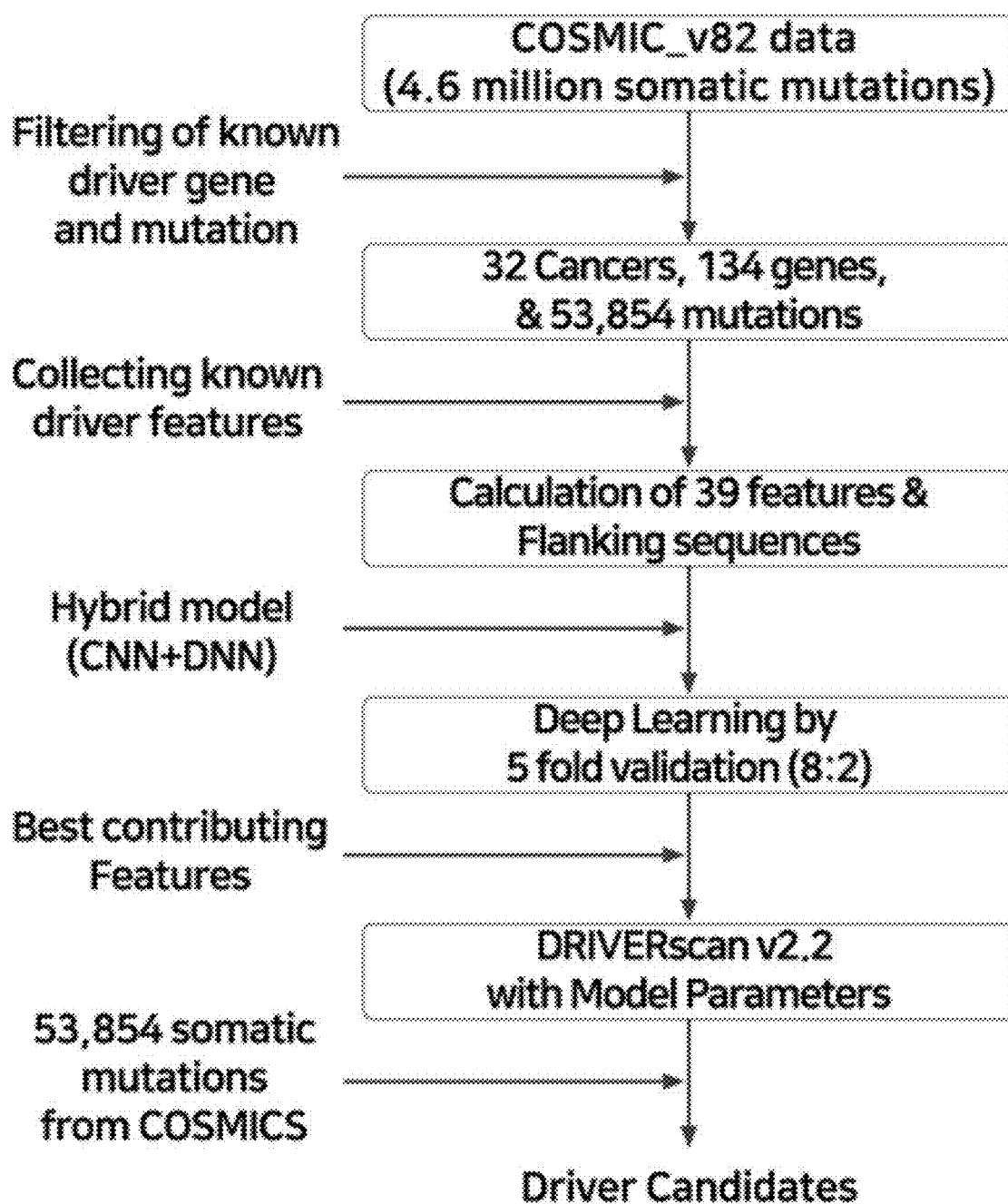

FIG. 13 illustrates an example of a process of detecting driver mutation biomarkers based on 1D strings according to a specific embodiment of the present invention.

Figure 14:
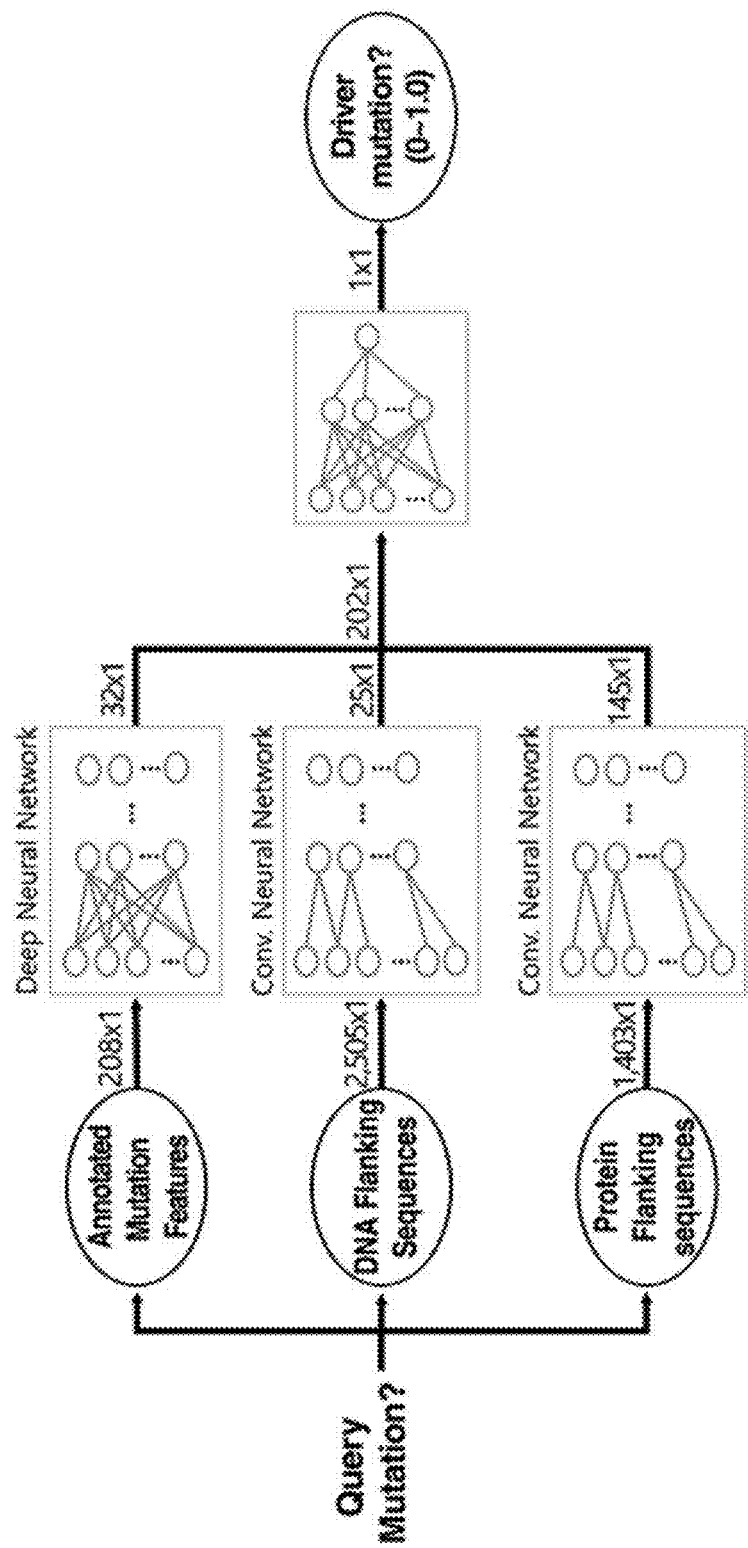

FIG. 14 illustrates an example of performing deep learning on driver mutation biomarkers based on 1D strings according to a specific embodiment of the present invention.

Figure 15:
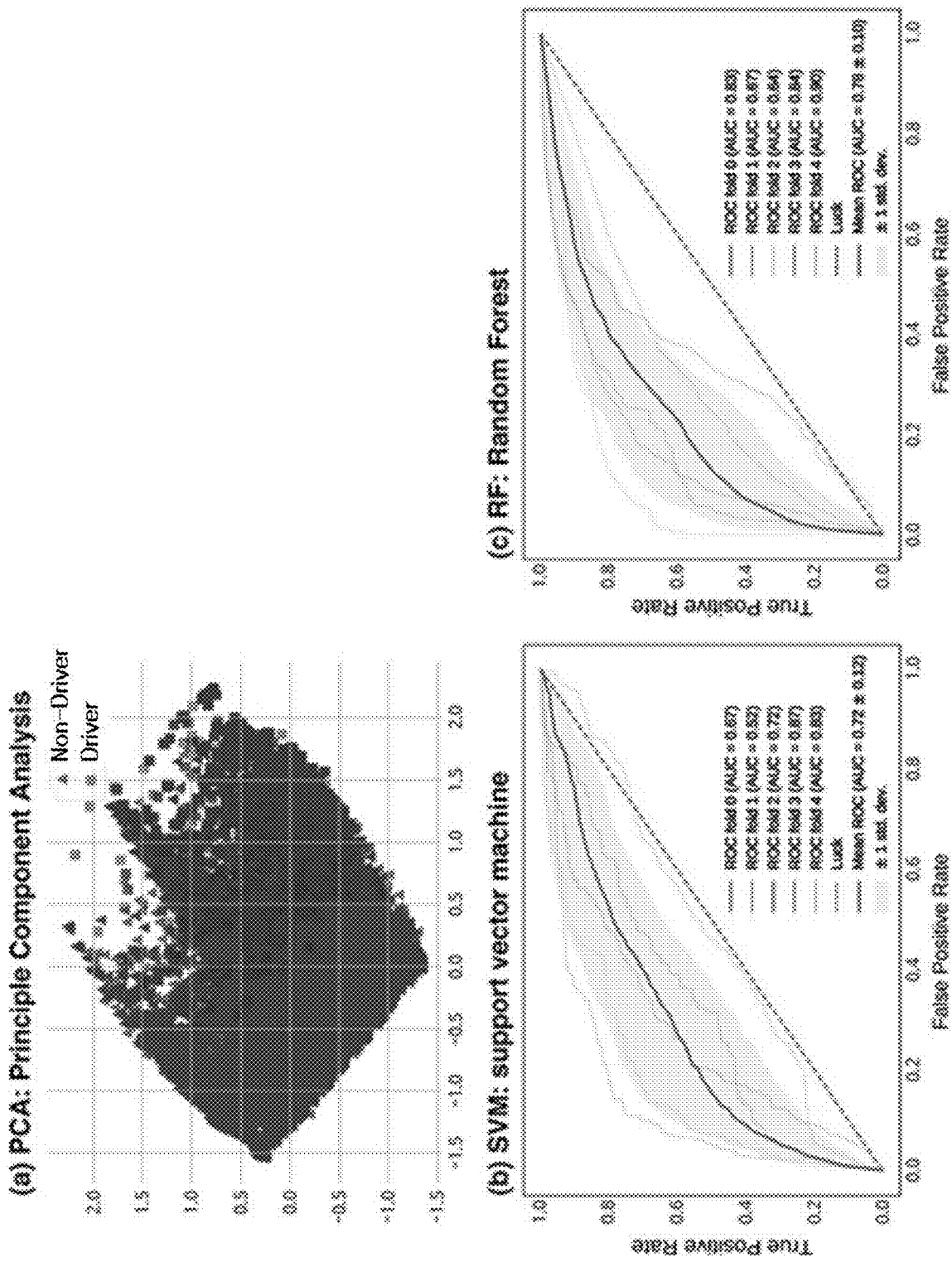

FIG. 15 illustrates standard classifiers (SVM & RF) for deep learning comparison based on 1D strings according to a specific embodiment of the present invention.

FIG. 16 illustrates an example of detecting deep learning driver mutation biomarkers based on 1D strings according to a specific embodiment of the present invention.

Figure 17:
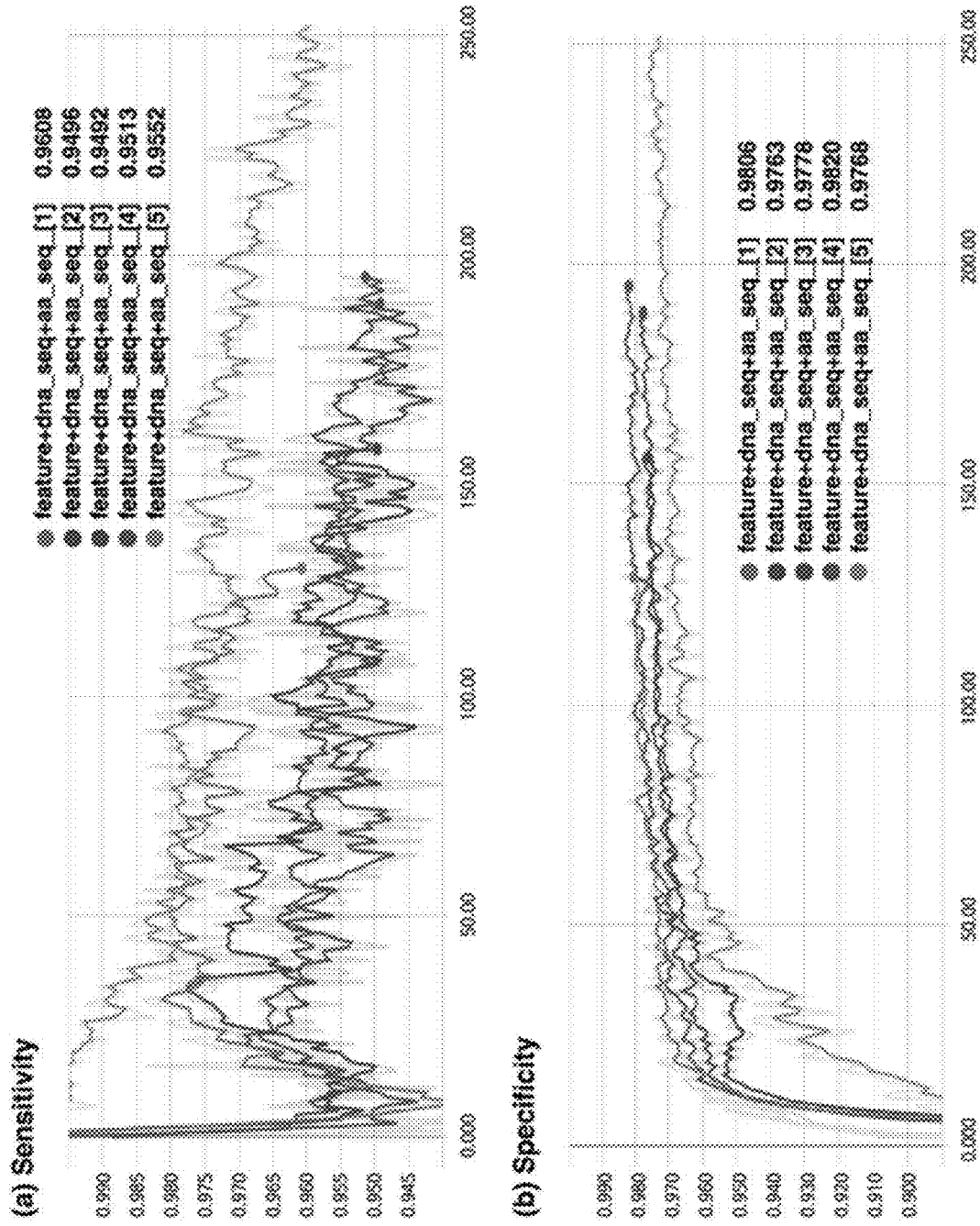

FIG. 17 illustrates an example of performing 5-fold verification of deep learning driver mutation biomarkers based on 1D strings according to a specific embodiment of the present invention.

Figure 18:
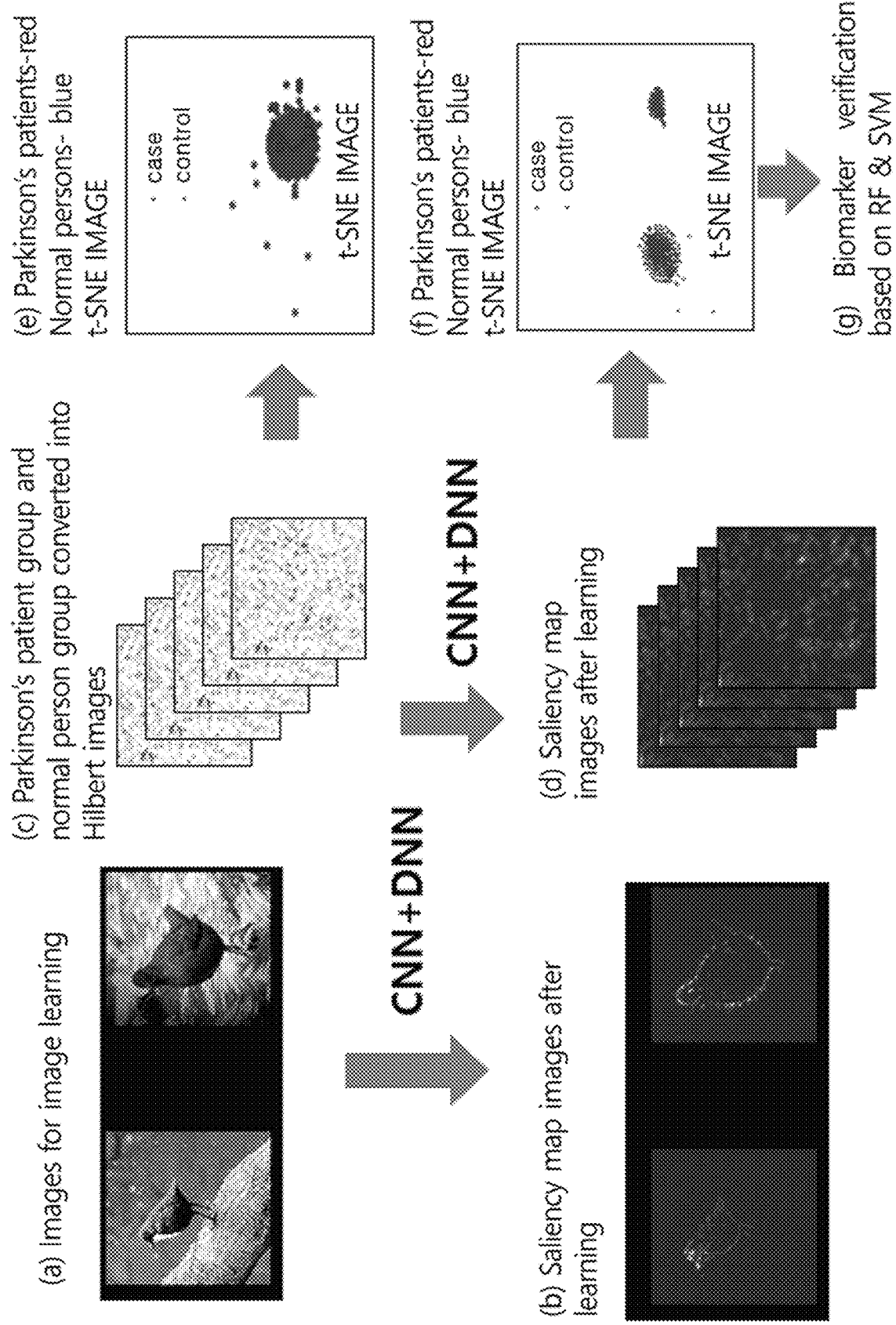

FIG. 18 illustrates an example of detecting patient stratification biomarkers and disease-associated biomarkers on the basis of 2D Hilbert images according to a specific embodiment of the present invention.

FIG. 19 illustrates an example of detecting patient stratification biomarkers and disease-associated biomarkers using three odds ratio models based on 2D Hilbert images according to a specific embodiment of the present invention.

DETAILED DESCRIPTION

Hereinafter, specific embodiments of a method of detecting biomarkers using an AI deep learning model for conversion data of populations according to the present invention will be described in detail with the accompanying drawings.

Figure 1:
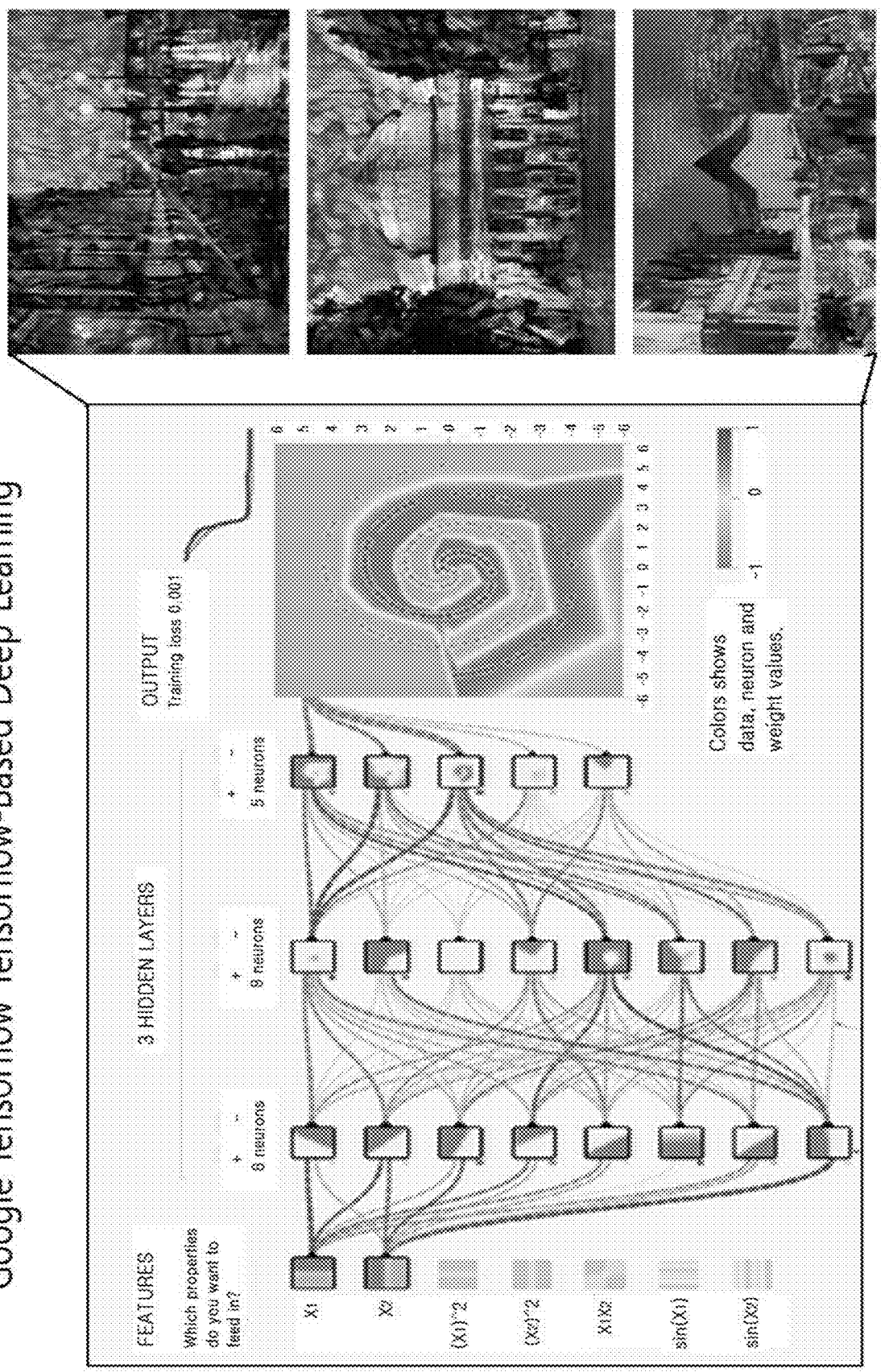
FIG. 1 illustrates an example of Google Tensorflow-based deep learning.
Figure 2:
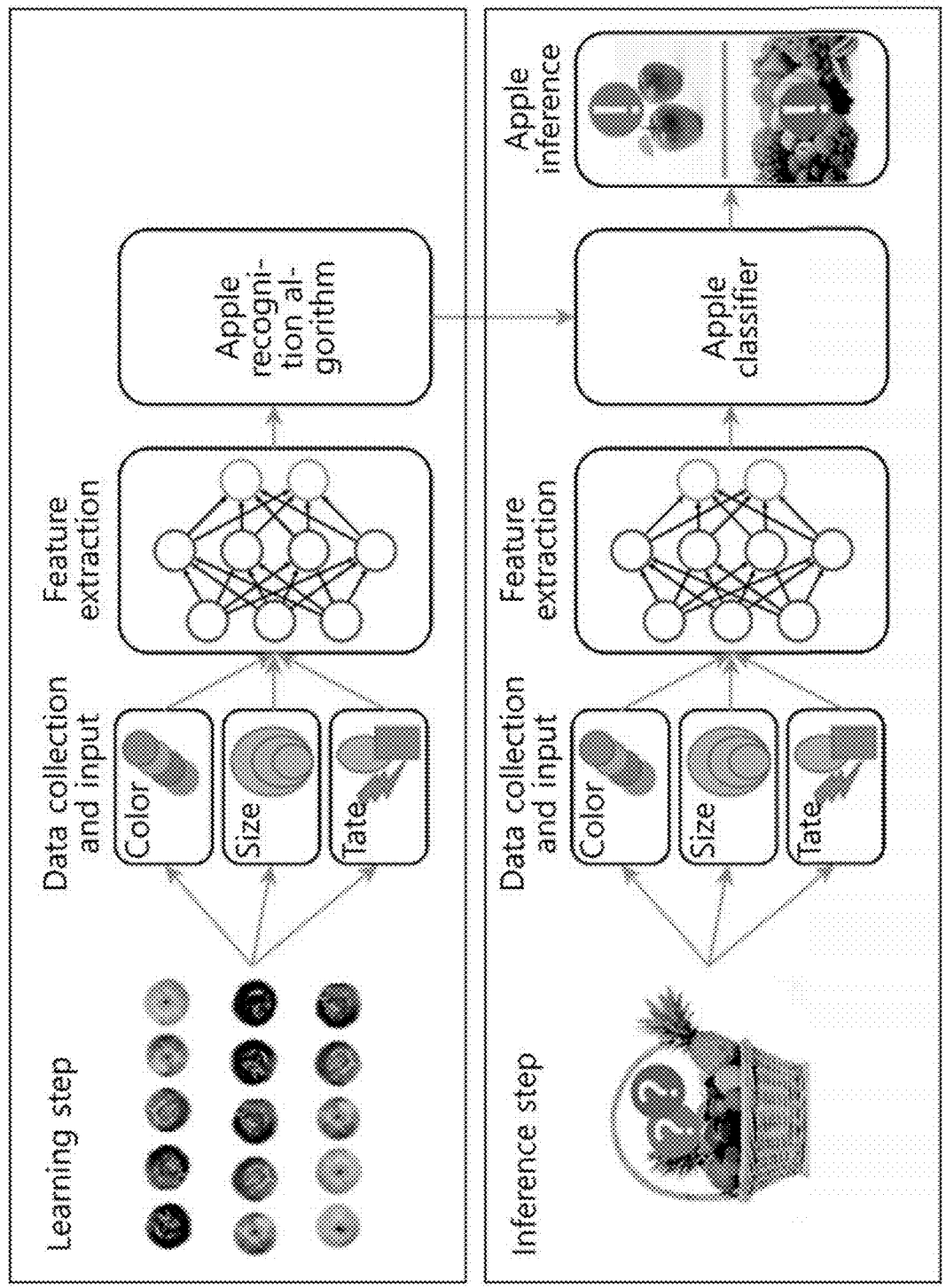
FIG. 2 illustrates an example of an AI deep learning model for apple classification.
Figure 3:
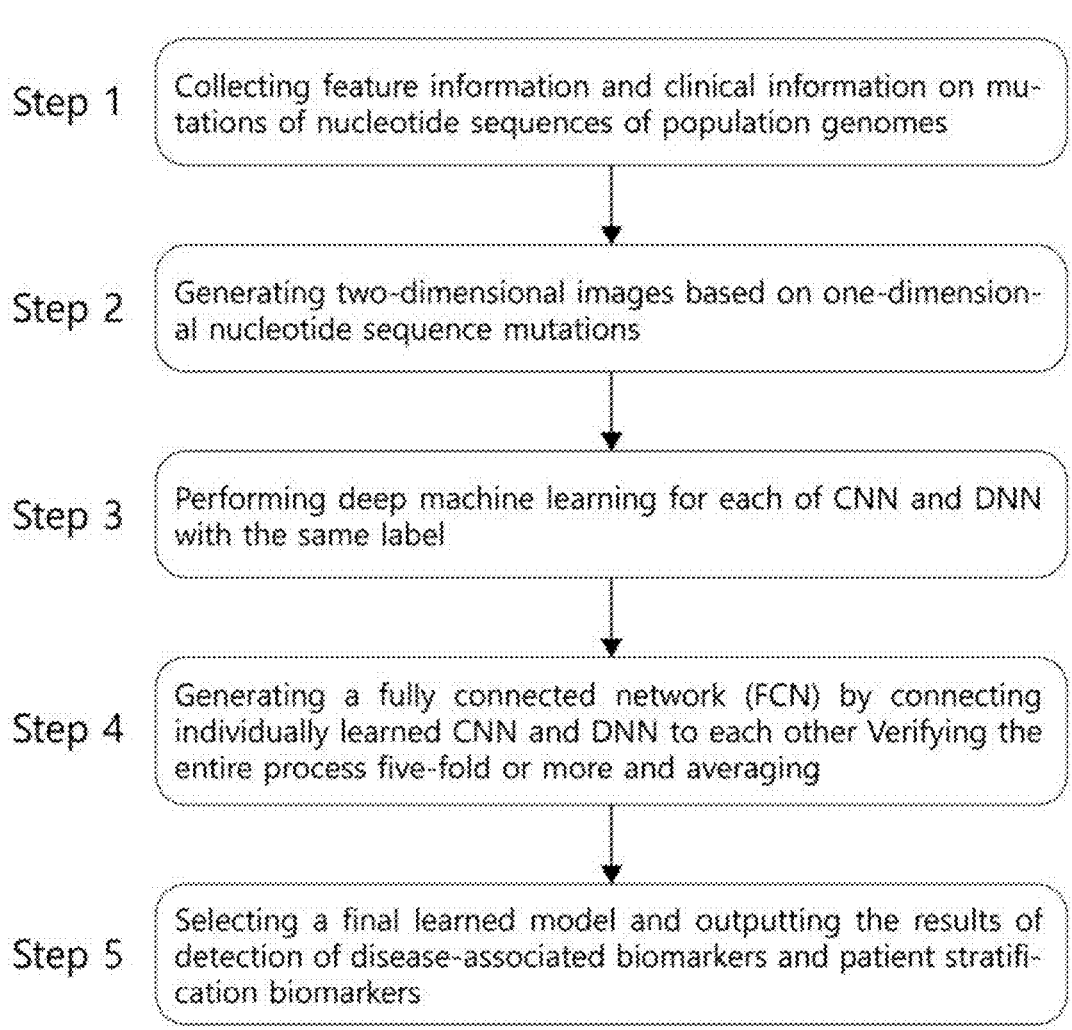
FIG. 3 is a flow chart illustrating a method for detecting biomarkers according to a specific embodiment of the present invention.
Figure 4:
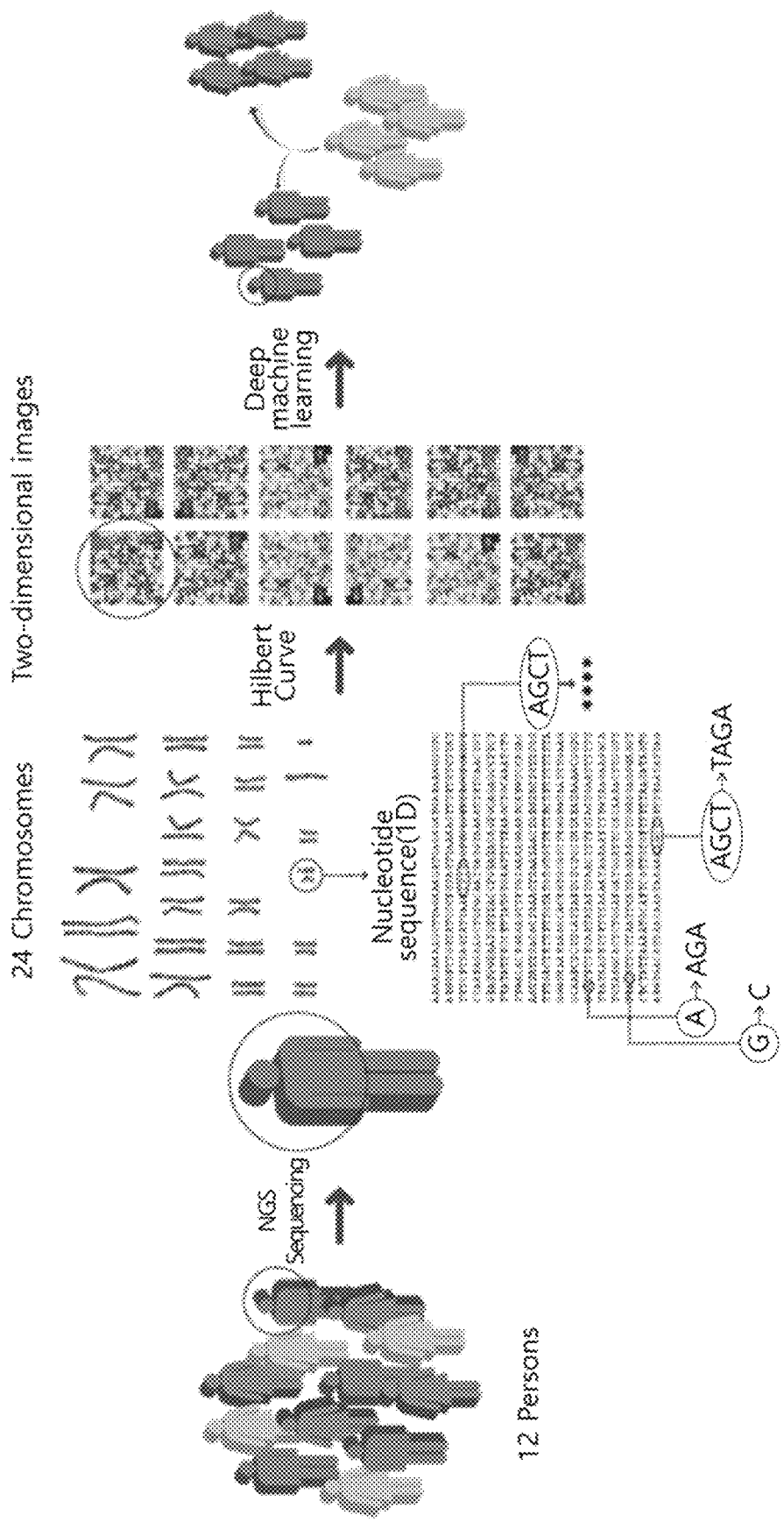
FIG. 4 illustrates an example of detecting patient stratification biomarkers according to the present invention.

FIG. 2 illustrates an example of an AI deep learning model for apple classification; FIG. 3 is a flow chart illustrating a method for detecting biomarkers according to a specific embodiment of the present invention; FIG. 4 illustrates an example of detecting patient stratification biomarkers according to the present invention; FIG. 5 illustrates an example of clinical information and phenotypes on a control group according to a specific embodiment of the present invention; FIG. 6 is a table showing an example of diploid mutation types of a control group according to a specific embodiment of the present invention; FIG. 7 schematically illustrates an example of diploid mutation types of a control group according to a specific embodiment of the present invention; FIG. 8 illustrates the mutation feature types and 1D strings of conversion data according to a specific embodiment of the present invention; FIG. 9 illustrates 3D structure profiles among the mutation feature types of conversion data according to a specific embodiment of the present invention; FIG. 10 illustrates an example of converting data into higher-dimensional images according to a specific embodiment of the present invention; FIG. 11 illustrates an example of generating the Hilbert curve according to a specific embodiment of the present invention; FIG. 12 illustrates a process of separating and combining CNN and DNN in a deep learning process according to a specific embodiment of the present invention; FIG. 13 illustrates an example of a process of detecting driver mutation biomarkers based on 1D strings according to a specific embodiment of the present invention; FIG. 14 illustrates an example of performing deep learning on driver mutation biomarkers based on 1D strings according to a specific embodiment of the present invention; FIG. 15 illustrates standard classifiers (SVM & RF) for deep learning comparison based on 1D strings according to a specific embodiment of the present invention; FIG. 16 illustrates an example of detecting deep learning driver mutation biomarkers based on 1D strings according to a specific embodiment of the present invention; FIG. 17 illustrates an example of performing 5-fold verification of deep learning driver mutation biomarkers based on 1D strings according to a specific embodiment of the present invention; FIG. 18 illustrates an example of detecting patient stratification biomarkers and disease-associated biomarkers on the basis of 2D Hilbert images according to a specific embodiment of the present invention; and FIG. 19 illustrates an example of detecting patient stratification biomarkers and disease-associated biomarkers using three odds ratio models based on 2D Hilbert images according to a specific embodiment of the present invention.

As shown in FIG. 2, deep learning will now be described using an example of an apple classifier. In a learning step, there are images of apples, and data on the features of the apples are collected and input. In addition, multilayer hyperparameters for extracting features on information about the color, size and taste of the apples are generated, and an algorithm (model) that learns and recognizes many fruits is generated.

In an inference step, apples are mixed with other fruits, including tangerine, kiwi, peach and the like. That is, from images of fruits (apple: label=1, and other fruits: label=0), information on color, size and taste is collected, and only the apples (label=1) are classified. In the present invention, 1D string, 2D image and 3D cubic conversion data of genome sequences and mutations correspond to various fruits (biomarker: label=1, and non-biomarker: label=0), and conversion data-based learning of the nucleotide sequences and mutations of many genomes is performed, and an AI deep learning model that recognizes a mutation corresponding to a biomarker (label=1) in the conversion data is generated.

Thus, when the method of the present invention is used, it is possible to detect only apples (biomarkers, label=1) among many fruits in the inference step.

As shown in FIGS. 3 and 4, the method for detecting biomarkers according to the present invention comprises the steps of: (1) collecting nucleotide sequence mutations and clinical information of population genomes; (2) generating conversion data by reflecting mutations of diploid genomes in the collected nucleotide sequences; (3) performing a deep learning model with the generated conversion data; (4) generating a fully connected network (FCN) in which the results obtained by the machine learning are linked; (4) performing selective verification; and (5) extracting biomarkers by the learned model.

Hereinafter, the technical features of each step of the method according to the present invention will be described in detail.

First, collection of nucleotide sequence mutations and clinical information in step (1) is performed using FASTQ, BAM (binary alignment map) and VCF (variant allele format), generated according to the GATK Best-practice which is the most standard method of an internationally recognized next-generation sequencing pipeline.

The population can be classified according to the type of disease or according to patient class. Namely, the population is classified according to whether a specific mutation in each genome based on driver mutation research is a driver mutation. If the specific mutation is a disease-associated biomarker, then the population is classified according to the type of disease, and if the biomarker is a biomarker which is involved in the stratification of responder patients, then the population is classified according to the class of responder patients or non-responder patients.

Collection of information on the nucleotide sequence mutations is performed using a known technique whose reliability was already proven, and the detailed description thereof is omitted herein.

FIG. 5 shows an example of collected clinical information.

In addition, FIG. 6 shows types of mutation information; FIG. 7 shows an actual example of mutation information; and FIG. 8 schematically illustrates mutation features and protein/DNA flanking sequences.

Figure 8A:
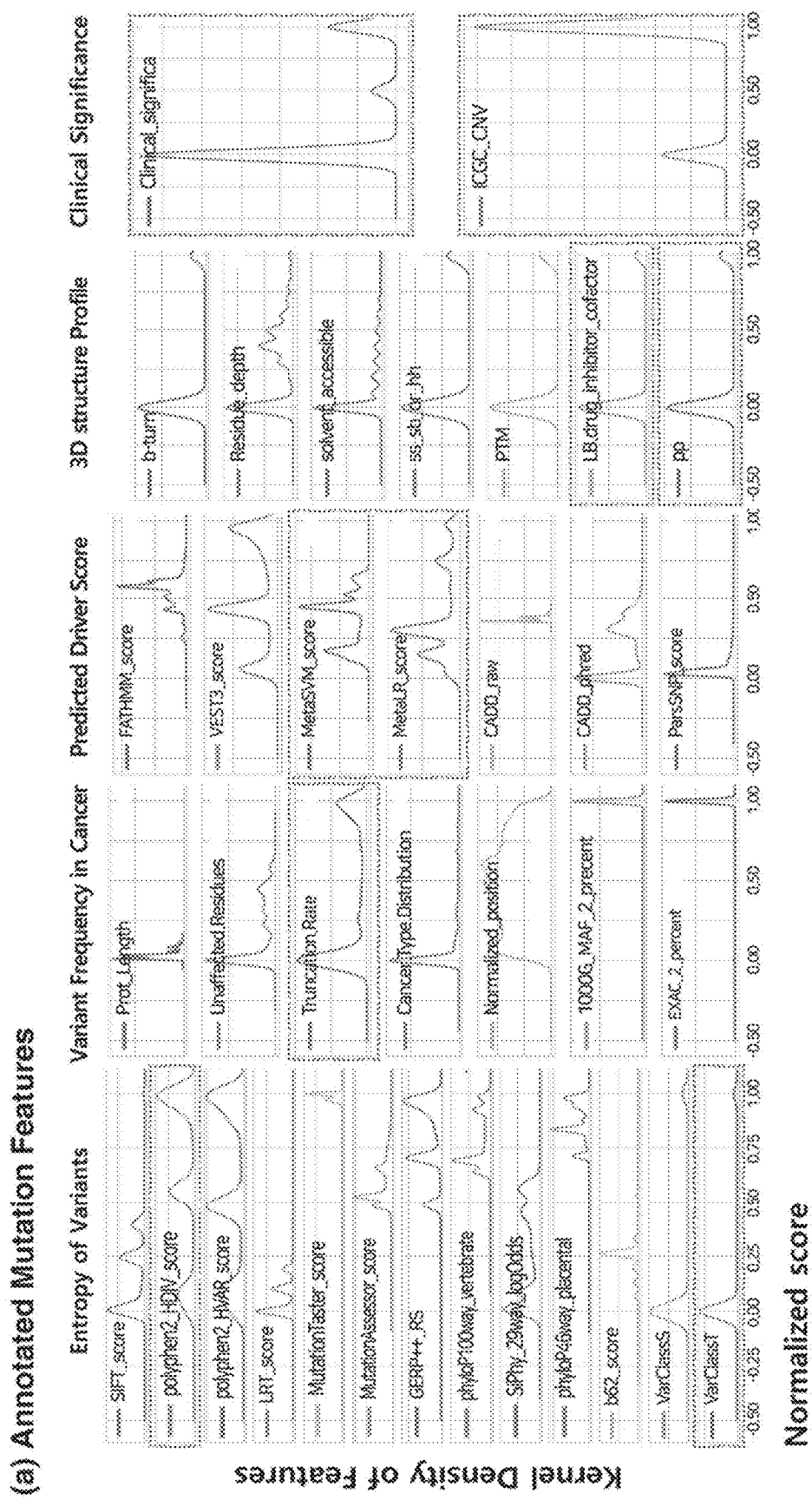

For the generation of conversion data in step (2), the conversion data may be conversion data for detecting biomarkers based on driver mutation research. In this case, annotated mutation features as shown in FIG. 8(a) are used as data for explaining 39 features, including entropy of variants in evolution of protein sequences or in multiple alignment maps, variant frequency in cancer, predicted driver score, 3D structure profile, and clinically significant mutation, etc.

In addition, for (b) DNA flanking sequences and (c) protein flanking sequences in FIG. 8, a DNA sequence consisting of 500 nucleotides disposed before and 500 nucleotides positioned after a mutation in the whole genome sequence in a 1D string format (500+500+1 =1001 nucleotides), or a protein (or peptide) sequence consisting of amino acids positioned before and 30 amino acids positioned after the mutation (30+30+1=61 amino acids), is defined as a 1D continuous sequence. In particular, FIG. 9 shows an example of the 3D structure profile shown in FIG. 8.

The generation of conversion data in disease association and patient stratification studies may comprise the steps of: i) generating a master template which is a locus template of unique mutations, which consists of an union of nucleotide mutations of population genomes; and ii) generating conversion data by converting each mutation of the master template and the population genomes into a set of unit data which is feature information expressed from the mutations.

First, the master template will now be described.

The master template is used as a standard for analysis in a machine learning process to be performed later, and comprises all mutations contained in population genomes.

Specifically, the master template comprises all mutations contained in the population genomes, but excludes redundant mutations, and the positions of all mutations contained in the population genomes are expressed.

Accordingly, in the method for detecting biomarkers according to the present invention, the biomarker makes it possible to learn the significance of each genome by the AI deep learning model, thereby detecting valid biomarkers.

Thus, the master template is individually generated for each classified unit of the population. Namely, the master template can be generated for the type of disease (cancer) and the type of patient class.

Meanwhile, as described above, if the master template is composed of all mutations contained in the population genomes, there is a possibility that the number of mutations becomes enormous and the resource consumption by analysis becomes excessive.

Accordingly, the master template can be generated to include valid mutations selected from among mutations of the population genomes according to the degree of redundancy in view of analysis efficiency.

In other words, in generation of the master template, mutations with a very low frequency in a particular disease patient group are highly likely to have a very low association with the disease, and these mutations are excluded from the master template. Likewise, mutations with a very low frequency in a normal group are highly likely to be personal mutations regardless of the disease, and thus these mutations are excluded from the master template. In particular, if mutations that appear multiple times in multiple samples of patients are absent or present in a very small number in normal people, the calculation of odds ratio or the like is performed to determine the ranking of risk allele mutations. In the opposite case, the calculation is performed to determine the ranking of protective mutations.

Now, the process of generating the conversion data will be described in detail. The conversion data are composed of unit data, and the unit data are configured to express feature information on each genetic mutation.

As shown in FIG. 8, the feature information refers to the various features of the mutations, which may be a variety of mutation-related information, including mutation types, mutation-associated factors, etc.

Meanwhile, the various structures and contents of the features are shown in FIG. 9.

Furthermore, the features may be expressed in various forms in unit data.

For example, the features may be expressed as the color of unit data (pixels), and a large number of the features may be expressed as channels. Namely, if deep learning is performed by a convolutional neural network (CNN), a large number of filters (k filters) having the same size may be used for single layers, which are independent of one another and are additionally learned via other filters after learning.

Here, k is the number of output channels. If the features are expressed as the color of unit data, the AI deep learning model process to be performed later is performed in a manner similar to an image learning process.

Meanwhile, the conversion data is completed by converting the unit data into a particular form. Specifically, as shown in FIG. 10, the unit data may be converted into a one-dimensional string form by one-dimensionally arranging them according to the nucleotide sequence.

Using this one-dimensional nucleotide flanking sequence string (FIG. 10*b*), a one-dimensional protein flanking sequence (FIG. 10*c*) and the feature of a mutation positioned in the center of the string, the generation of a model for predicting cancer/rare disease is performed.

Now, a process of generating two-dimensional image conversion data which are used in responder patient stratification and disease association research for information on gene-gene interactions will be described in detail. The conversion data are composed of a combination of unit data, and the unit data may be configured as described below so as to express the feature of each genetic mutation.

Namely, using (i) the whole nucleotide sequence, (ii) only disease risk mutations and disease protective mutations in the same number, or (iii) only risk mutations, conversion data consisting of a two-dimensional image of 1024*1024=1,048,576 or more pixels corresponding to nucleotide sequences or mutations may be generated from a two-dimensional image of 32*32=1024 pixels corresponding to nucleotide sequences or mutations.

At this time, the two-dimensional image may be generated using various arrangement methods, but may preferably generated by the Hilbert curve method or the fractal curve method.

What is important here is that an image obtained by arranging all conversion data on mutations of the master template and mutations of the population genome used in learning with the same regularity should be applied. However, the sequence of mutations in the genome can be changed according to the purpose of detection. It is possible to make and use In other words, you can make Hilbert and Fractal curves in which the sequence of chromosome units, gene units or specific functional gene group units is changed according to the required purpose.

Meanwhile, the conversion data may be generated as a three-dimensional form by sequentially arranging the two-dimensional image form of the conversion data in a three-dimensional space.

The various forms of the conversion data are set in consideration of the learning efficiency according to the size of the conversion data.

Namely, in the case of driver mutation biomarkers (cancer/rare disease mutations) with a relatively small amount of the conversion data (the number of mutations and the number of features of the mutations), the conversion data are used in a one-dimensional string form. In addition, as the amount of the conversion data increases due to the use of the genomic data of a disease case group and a normal control group, like the case of responder patient stratification and drug association research, the conversion data are used in a two- or three-dimensional form.

Next, in step (3), as shown in FIG. 12, the AI deep learning model process with the conversion data is performed by comparing the conversion data of mutations of each population genome with the conversion data of the master template.

At this time, the AI deep learning model process with the conversion data learns mutations of the master template with mutations of the population genome by any one or more algorithms of Convolutional Neural Network (CNN), Deep Neural Network (DNN) and Recurrent Neural Network (RNN).

At this time, the AI deep learning model process may be performed by any one of CNN, DNN and RNN, it may also be performed by two or more algorithms of CNN, DNN and RNN, and the results of the learning may be connected to generate a network.

Namely, in the step of generating the network (step (4)), the AI deep learning model process is performed by two or more algorithms of CNN, DNN and RNN, and the results of the learning are connected to generate a fully connected network (FCN).

FIG. 12 illustrates an example of this AI deep learning model process in which learning data are generated by Convolutional Neural Network (CNN) and Deep Neural Network (DNN) and separated.

In other words, the results learned by various deep learning methods are connected to one another according to the relationship, thereby generating a single network.

Meanwhile, the method of the present invention may further comprise a step of verifying either the master template learned by the above-described process or a network thereof. In other words, the accuracy of learning can be verified by comparing the extent to which biomarkers were expressed on the learned master template.

Meanwhile, in the step of extracting biomarkers (step (5)), genome mutations resulting from the learning are extracted as biomarkers and summarized, after the learned master template has been verified to have a certain accuracy.

An example of detecting these driver mutation biomarkers is FIGS. 13 to 17. Specifically, FIG. 13 is a flow chart showing collecting data for detection of driver mutation biomarkers from public cancer genome data (COSMIC) and detecting final driver mutations. FIG. 14 shows a deep learning layer model employing data corresponding to those shown in FIG. 13. It shows a model in which mutation is input in a query step and whether or not the mutation is a driver mutation is determined. FIG. 5 shows the results of performing 5-fold verification using standard classifier (SVM and RF) for comparison and comparing the verification results with the deep learning results.

These detected biomarkers may be of various types depending on the type of learning. For example, the biomarkers may be either disease-associated biomarkers or biomarkers that are involved in patient stratification. FIG. 16 shows features that contribute to the detection of driver mutation biomarkers. As shown therein, the driver mutation f1-scores are 88% for features, 70% for DNA flanking sequences, 67% for protein flanking sequences, and 91% for a hybrid model. This indicates that the hybrid model has the best performance. In addition, FIG. 17 shows that the sensitivity and specificity of 5-fold verification are above 95% on average.

In addition, examples of detecting disease-associated biomarkers and biomarkers for stratification of responder patients are shown in FIGS. 18 and 19.

As shown in FIG. 18a, sparrow images are learned using Convolutional Neural Network (CNN) and Deep Neural Network (DNN), and as shown in FIG. 18b, a Saliency map image (Non-Patent Document 32) after learning is generated, and the outline of the bird is calculated.

In the same manner, as shown in FIG. 18c, Hilbert curve 2D images are generated using converted data. Here, from the genomic data of 400 Parkinson's patients and 200 normal people, Hilbert curve 2D images (256*256=65,536) were generated. Pixels in each image were generated by selecting risk mutations and protective mutations in half. As shown in FIG. 18d, Saliency map images (Non-Patent Documents 32) were generated, and as shown in FIG. 18e, t-SNE images (Non-Patent Document 31) were generated, and patient stratification was performed.

Meanwhile, FIG. 18e shows the results of t-SNE (Document 31) prior to deep learning, and indicates that patient stratification was not good in the absence of learning. FIG. 18f shows the results of t-SNE after deep learning, and indicates that Parkinson's patients were completely separated from normal people. In addition, as shown in FIG. 18g, the performance of the detected driver mutation biomarkers that substantially contributed to patient stratification can be verified using SVM (Non-Patent Document 34) and RF (Non-Patent Document 33), after the biomarkers have been detected.

FIG. 19 shows the results of comparing three different odds ratio methods for the patient stratification biomarkers detected as shown in FIG. 18, and indicates that the accuracy of patient stratification in Odds Ratio_b is 92%. The remaining Odds Ratio_a and Odds Ratio_c show 86% and 87%, respectively. This suggests that the accuracy of patient stratification based on Odds Ratio_b is the highest.

The present invention relates to a method and a system for detecting disease-associated biomarkers and biomarkers for patient stratification research with increased accuracy and efficiency in order to identify human genetic features. The system and method comprise converting the nucleotide sequences of population genomes into two-dimensional images and applying Google Tensorflow-based deep learning technology to the two-dimensional image. According to the present invention, when 3 billion one-dimensional nucleotides are expressed as two-dimensional images, it is possible to efficiently biomarkers associated with diseases caused by multiple gene mutations (including gene-gene interactions), such as complex diseases (diabetes, hypertension, osteoporosis, etc.), as well as biomarkers for patient stratification research. In the case of the human genome, calculation by CNN employing deep learning two-dimensional images is 54,000-fold faster than analysis performed using a one-dimensional form of three billion nucleotides, and analysis performed using three-dimensional images is about 1,400-fold faster than analysis performed using two-dimensional images, and the accuracy is improved. Therefore, the present invention can be a very important breakthrough in personalized medicine in the field of genome analysis, and can have a great effect on the domestic and foreign medical industries.

As described above, the system and method of detecting driver mutation biomarkers, disease-associated biomarkers and patient stratification biomarkers according to the present invention may exhibit the following effects. That is, according to the present invention, data converted in consideration of gene-gene interactions in each of population genomes can be analyzed, unlike a conventional method in which nucleotides and mutations are aligned in a multiple alignment and the aligned locus mutation units are analyzed. Therefore, according to the present invention, the performance of detection of driver mutation biomarkers, disease-associated biomarkers and patient stratification biomarkers can be improved.

In addition, according to the present invention, verified deep learning technology in Google's Tensorflow-based high-dimensional environments can be used instead of genome sequencing. Thus, the program can be advanced, and the speed and accuracy of analysis can be dramatically improved.

The scope of the present invention is not limited to the embodiments described above and should be defined by the appended claims.

Those skilled in the art will appreciate that various changes and modifications are possible without departing from the scope of the present invention as defined by the appended claims.

---

What is claimed is:

1. A method of detecting biomarkers using an artificial intelligence (AI) deep learning model for conversion data of nucleotide sequences and mutations of population genomes, the method comprising the steps of:
   (A) collecting nucleotide sequences and mutations of population genomes;
   (B) generating conversion data by reflecting mutations of diploid genomes in the collected nucleotide sequences;
   (C) performing an artificial intelligence (AI) deep learning model with the generated conversion data, wherein the deep learning model comprises two or more algorithms selected from the group consisting of a Convolutional Neural Network (CNN), a Deep Neural Network (DNN), and a Recurrent Neural Network (RNN);
   (D) generating a fully connected network (FCN) by connecting results obtained by the two or more algorithms; and
   (E) extracting biomarkers from the FCN, thereby detecting them,
   wherein the population is classified according to a type of disease or a class of patients, and
   wherein the biomarkers are biomarkers for stratification of responder patients and disease-associated biomarkers, and the generating of the conversion data in step (B) comprises steps of:
   (B2-1) generating a master template which is a locus template of unique mutations, which consists of a union of the nucleotide sequence mutations of the population genomes;
   (B2-2) generating conversion data by converting the mutations of the master template and the population genomes into a set of unit data expressed as feature information;
   (B2-3) selecting risk allele or protective allele mutations;
   (B2-4) making two-dimensional images of nucleotide sequences or mutations from a whole of the risk allele and protective allele mutations, or the risk allele mutations and the protective allele mutations in a same number, or only the risk allele mutations; and
   (B2-5) filtering whether or not the biomarkers selected in step (B2-4) above are present in public mutation data for use as biomarkers.

2. The method of claim 1, wherein the collecting of the nucleotide sequences and mutations of population genomes in step (A) comprises generating the nucleotide sequences of the genomes from next-generation sequencing data in a form of FASTQ BAM (binary alignment map) or VCF (variant allele format).

3. The method of claim 2, wherein feature information on the biomarkers is expressed as a color of unit data (pixel), characters, or a combination thereof.

4. The method of claim 1, wherein conversion data in a one-dimensional string form are generated by arranging unit data according to the nucleotide sequence.

5. The method of claim 1, wherein the artificial intelligence (AI) learning model in step (C) is performed by comparing the conversion data of the mutations of each population genome based on the conversion of the master template.

6. The method of claim 5, wherein the master template is generated with valid mutations selected from among the mutations of the population genomes according to a degree of redundancy.

7. The method of claim 1, further comprising a step of verifying the extracted biomarkers using known biomarkers.

8. The method of claim 1, wherein the selecting of the mutations in step (B2-3) is performed by selecting the mutations in descending order of an odds ratio of the risk alleles or the protective alleles.

9. The method of claim 8, wherein the risk allele or protective allele mutations are expressed as a color of unit data (pixel), characters, or a combination thereof.

10. A method of detecting biomarkers using an artificial intelligence (AI) deep learning model for conversion data of nucleotide sequences and mutations of population genomes, the method comprising the steps of:
  (A) collecting nucleotide sequences and mutations of population genomes;
  (B) generating conversion data by reflecting mutations of diploid genomes in the collected nucleotide sequences;
  (C) performing an artificial intelligence (AI) deep learning model with the generated conversion data, wherein the deep learning model comprises two or more algorithms selected from the group consisting of a Convolutional Neural Network (CNN), a Deep Neural Network (DNN), and a Recurrent Neural Network (RNN);
  (D) generating a fully connected network (FCN) by connecting results obtained by the two or more algorithms; and
  (E) extracting biomarkers from the FCN, thereby detecting them,
  wherein the population is classified according to a type of disease or a class of patients,
  wherein the conversion data are in a two-dimensional image form generated by arranging conversion data of a one-dimensional string form into the two-dimensional image form by a Hilbert-curve method.

11. A method of detecting biomarkers using an artificial intelligence (AI) deep learning model for conversion data of nucleotide sequences and mutations of population genomes, the method comprising the steps of:
  (A) collecting nucleotide sequences and mutations of population genomes;
  (B) generating conversion data by reflecting mutations of diploid genomes in the collected nucleotide sequences;
  (C) performing an artificial intelligence (AI) deep learning model with the generated conversion data, wherein the deep learning model comprises two or more algorithms selected from the group consisting of a Convolutional Neural Network (CNN), a Deep Neural Network (DNN), and a Recurrent Neural Network (RNN);
  (D) generating a fully connected network (FCN) by connecting results obtained by the two or more algorithms; and
  (E) extracting biomarkers from the FCN, thereby detecting them,
  wherein the population is classified according to a type of disease or a class of patients,
  wherein the conversion data are in a three-dimensional cubic form generated by sequentially arranging conversion data of a two-dimensional image form into the three-dimensional cubic form.

12. A method of detecting biomarkers using an artificial intelligence (AI) deep learning model for conversion data of nucleotide sequences and mutations of population genomes, the method comprising the steps of:
  (A) collecting nucleotide sequences and mutations of population genomes;
  (B) generating conversion data by reflecting mutations of diploid genomes in the collected nucleotide sequences;
  (C) performing an artificial intelligence (AI) deep learning model with the generated conversion data, wherein the deep learning model comprises two or more algorithms selected from the group consisting of a Convolutional Neural Network (CNN), a Deep Neural Network (DNN), and a Recurrent Neural Network (RNN);
  (D) generating a fully connected network (FCN) by connecting results obtained by the two or more algorithms; and
  (E) extracting biomarkers from the FCN, thereby detecting them,
    wherein the population is classified according to a type of disease or a class of patients, and
    wherein the biomarkers are biomarkers for stratification of responder patients and disease-associated biomarkers, and the generating of the conversion data in step (B) comprises steps of:
      generating a master template which is a locus template of unique mutations, which consists of a union of the nucleotide sequence mutations of the population genomes;
      generating conversion data by converting the mutations of the master template and the population genomes into a set of unit data expressed as feature information; and
      making two-dimensional images of nucleotide sequences.

* * * * *

SEQUENCE LISTING

<160> NUMBER OF SEQ ID NOS: 27

<210> SEQ ID NO 1
<211> LENGTH: 13
<212> TYPE: DNA
<213> ORGANISM: Artificial Sequence
<220> FEATURE:
<223> OTHER INFORMATION: Synthetic nucleotide

<400> SEQUENCE: 1
gagagacgac gac                                                        13

<210> SEQ ID NO 2
<211> LENGTH: 35
<212> TYPE: DNA
<213> ORGANISM: Artificial Sequence -continued
<220> FEATURE:
<223> OTHER INFORMATION: Synthetic nucleotide

<400> SEQUENCE: 2
gcaaggggta acttccagca tggccacact gacgt                35

<210> SEQ ID NO 3
<211> LENGTH: 35
<212> TYPE: DNA
<213> ORGANISM: Artificial Sequence
<220> FEATURE:
<223> OTHER INFORMATION: Synthetic nucleotide

<400> SEQUENCE: 3
ggggtcatgc tgccatgctg tggggttaag cctgc                35

<210> SEQ ID NO 4
<211> LENGTH: 37
<212> TYPE: DNA
<213> ORGANISM: Artificial Sequence
<220> FEATURE:
<223> OTHER INFORMATION: Synthetic nucleotide

<400> SEQUENCE: 4
tctggtaaag caggtagctt ttttcaggtt attatag              37

<210> SEQ ID NO 5
<211> LENGTH: 35
<212> TYPE: DNA
<213> ORGANISM: Artificial Sequence
<220> FEATURE:
<223> OTHER INFORMATION: Synthetic nucleotide

<400> SEQUENCE: 5
gactgatcgg tggggatggt tgggatcctt ggatc                35

<210> SEQ ID NO 6
<211> LENGTH: 35
<212> TYPE: DNA
<213> ORGANISM: Artificial Sequence
<220> FEATURE:
<223> OTHER INFORMATION: Synthetic nucleotide

<400> SEQUENCE: 6
ccagctgcgg ggctcccact gccagccgct gagac                35

<210> SEQ ID NO 7
<211> LENGTH: 41
<212> TYPE: PRT
<213> ORGANISM: Artificial Sequence
<220> FEATURE:
<223> OTHER INFORMATION: Synthetic peptide

<400> SEQUENCE: 7

Gly His Glu Phe Val Phe Leu Leu Lys Gly His Met Gln Leu Phe Gly
1               5                   10                  15

Leu Val Asn Thr Leu Leu Ala Asn Asp Pro Thr Ser Leu Arg Lys Asn
            20                  25                  30

Leu Ser Ile Gln Arg Ala Cys Gly Thr
        35                  40

<210> SEQ ID NO 8
<211> LENGTH: 42
<212> TYPE: PRT
<213> ORGANISM: Artificial Sequence
<220> FEATURE:
<223> OTHER INFORMATION: Synthetic peptide

<400> SEQUENCE: 8

Lys Thr Leu Lys Ala Gly Tyr Thr Glu Lys Gln Met Gly Gln Phe Ser
1               5                   10                  15

His His Asn Ile Ile Arg Leu Glu Gly Val Ile Ser Lys Tyr Lys Pro
            20                  25                  30

Met Met Ile Ile Thr Gly Val Ile Ser Lys
        35                  40

<210> SEQ ID NO 9
<211> LENGTH: 41
<212> TYPE: PRT
<213> ORGANISM: Artificial Sequence
<220> FEATURE:
<223> OTHER INFORMATION: Synthetic peptide

<400> SEQUENCE: 9

Lys Arg Val Lys Asp Ser Asp Asp Val Pro Leu Pro Thr Arg Thr Val
1               5                   10                  15

Asp Thr Lys Gln Ala His Glu Leu Ala Lys Ser Tyr Gly Ile Pro Phe
            20                  25                  30

Ile Glu Thr Ser Ala Lys Asp Ser Asp
        35                  40

<210> SEQ ID NO 10
<211> LENGTH: 42
<212> TYPE: PRT
<213> ORGANISM: Artificial Sequence
<220> FEATURE:
<223> OTHER INFORMATION: Synthetic peptide

<400> SEQUENCE: 10

Met Thr Ala Ile Ile Lys Glu Ile Val Ser Gly Phe Asp Leu Asp Leu
1               5                   10                  15

Thr Tyr Ile Tyr Pro Asn Ile Ile Ala Met Gly Phe Pro Ala Glu Arg
            20                  25                  30

Leu Glu Gly Val Tyr Arg Leu Asp Leu Thr
        35                  40

<210> SEQ ID NO 11
<211> LENGTH: 41
<212> TYPE: PRT
<213> ORGANISM: Artificial Sequence
<220> FEATURE:
<223> OTHER INFORMATION: Synthetic peptide

<400> SEQUENCE: 11

Asp Asn Pro Glu Tyr Ser Pro Asp Pro Ser Ile Leu Asp Leu Trp Gln
1               5                   10                  15

Val Lys Ser Gly Thr Ile Phe Asp Asn Phe Leu Ile Thr Asn Asp Glu
            20                  25                  30

Ala Tyr Ala Glu Glu Trp Gln Val Lys
        35                  40

<210> SEQ ID NO 12
<211> LENGTH: 15
<212> TYPE: DNA
<213> ORGANISM: Artificial Sequence
<220> FEATURE:
<223> OTHER INFORMATION: Synthetic nucleotide

<400> SEQUENCE: 12
tcatatgcac cccgt                                                      15

<210> SEQ ID NO 13
<211> LENGTH: 15
<212> TYPE: DNA
<213> ORGANISM: Artificial Sequence
<220> FEATURE:
<223> OTHER INFORMATION: Synthetic nucleotide

<400> SEQUENCE: 13
tcatatgcac cacgt                                                      15

<210> SEQ ID NO 14
<211> LENGTH: 15
<212> TYPE: DNA
<213> ORGANISM: Artificial Sequence
<220> FEATURE:
<223> OTHER INFORMATION: Synthetic nucleotide

<400> SEQUENCE: 14
tcatatgcat atcgt                                                      15

<210> SEQ ID NO 15
<211> LENGTH: 21
<212> TYPE: DNA
<213> ORGANISM: Artificial Sequence
<220> FEATURE:
<223> OTHER INFORMATION: Synthetic nucleotide

<400> SEQUENCE: 15
tcatatacgt atgcaccacg t                                               21

<210> SEQ ID NO 16
<211> LENGTH: 27
<212> TYPE: DNA
<213> ORGANISM: Artificial Sequence
<220> FEATURE:
<223> OTHER INFORMATION: Synthetic nucleotide

<400> SEQUENCE: 16
acgtacgtgt acgtacgtaa cgtacgt                                         27

<210> SEQ ID NO 17
<211> LENGTH: 11
<212> TYPE: DNA
<213> ORGANISM: Artificial Sequence
<220> FEATURE:
<223> OTHER INFORMATION: Synthetic nucleotide

<400> SEQUENCE: 17
agaagtagag g                                                          11

<210> SEQ ID NO 18
<211> LENGTH: 12
<212> TYPE: DNA
<213> ORGANISM: Artificial Sequence
<220> FEATURE:
<223> OTHER INFORMATION: Synthentic nucleotide

<400> SEQUENCE: 18
agaagttaga gg                                                         12

<210> SEQ ID NO 19
<211> LENGTH: 154

```
<212> TYPE: DNA
<213> ORGANISM: Artificial Sequence
<220> FEATURE:
<223> OTHER INFORMATION: Synthetic nucleotide

<400> SEQUENCE: 19
gaaaaggacc tcccaggcca gtgccgggcg gcaggaaggc gcacaaaagg aggaagaagg      60
cgcaggaagg cgcacccgaa aaggacctcc caggccagtg ccgggcggca ggaaggcgca     120
caaaaggagg aagaaggcgc aggaaggcgc accc                                 154

<210> SEQ ID NO 20
<211> LENGTH: 140
<212> TYPE: DNA
<213> ORGANISM: Artificial Sequence
<220> FEATURE:
<223> OTHER INFORMATION: Synthetic nucleotide

<400> SEQUENCE: 20
ccattgtccc ccggcctcct ctgccctgcc cctggagggt gcggcaggaa taaggaaaag      60
gacctcccag gccagtgccg ggcggcagga aggcgcaccc aggaacttct tctggaagac     120
cgcaagttta attacagacc                                                 140

<210> SEQ ID NO 21
<211> LENGTH: 148
<212> TYPE: DNA
<213> ORGANISM: Artificial Sequence
<220> FEATURE:
<223> OTHER INFORMATION: Synthetic nucleotide

<400> SEQUENCE: 21
gctgctgctg ctctccgggg ccaccggccg agacagcgag ctcctgactt tcctcgcttg      60
cctcatagga gaggaagctc agcaatccgc gcgccgggac tcctcctgca aataaaacct     120
caccaccgac aagccaggcg agaatgcc                                        148

<210> SEQ ID NO 22
<211> LENGTH: 140
<212> TYPE: DNA
<213> ORGANISM: Artificial Sequence
<220> FEATURE:
<223> OTHER INFORMATION: Synthetic nucleotide

<400> SEQUENCE: 22
aggaacttct tctggaagac ggcggcagga aggcgcaccc gacctcccag gccagtgccg      60
gcggcaggaa taaggaaaag ctgccctgcc cctggagggt gatgccattg tccccggcc     120 ggcggcagga aggcgcaccc                                                 140

<210> SEQ ID NO 23
<211> LENGTH: 144
<212> TYPE: DNA
<213> ORGANISM: Artificial Sequence
<220> FEATURE:
<223> OTHER INFORMATION: Synthetic nucleotide

<400> SEQUENCE: 23
tcctcctgca aataaaacct caccagcaat ccgcgcgccg ggaccctcat aggagaggaa      60
gctcctcctg actttcctcg cttgccaccg gccgagacag catagctgct gctgctctcc     120 gggggcggc aggaaggcgc accc                                             144

<210> SEQ ID NO 24
```

```
<211> LENGTH: 60
<212> TYPE: DNA
<213> ORGANISM: Artificial Sequence
<220> FEATURE:
<223> OTHER INFORMATION: Synthetic nucleotide

<400> SEQUENCE: 24
gagcaaagac acaaagaccg ccattgtcca cacatgatag gtgagacaaa gcgttagagc    60

<210> SEQ ID NO 25
<211> LENGTH: 60
<212> TYPE: DNA
<213> ORGANISM: Artificial Sequence
<220> FEATURE:
<223> OTHER INFORMATION: Synthetic nucleotide

<400> SEQUENCE: 25
gtcaacagac gcaaagagtg aaaggttcca cgtgtacata gtgcgacaga acgacccacg    60

<210> SEQ ID NO 26
<211> LENGTH: 64
<212> TYPE: DNA
<213> ORGANISM: Artificial Sequence
<220> FEATURE:
<223> OTHER INFORMATION: Synthetic nucleotide

<400> SEQUENCE: 26
tacacacaac gtacaaggtg catgacaaaa tgcgccagtg catgcgagga taaagcacaa    60
ggtg                                                                64

<210> SEQ ID NO 27
<211> LENGTH: 64
<212> TYPE: DNA
<213> ORGANISM: Artificial Sequence
<220> FEATURE:
<223> OTHER INFORMATION: Synthetic nucleotide

<400> SEQUENCE: 27
gatgacaaac gtgtggaaca aatgcacaac aaacgcattg gtgcgtcaga tacacaaccg    60
cgtg                                                                64
```